United States Patent [19]

Allen, III

[11] Patent Number: 4,731,726

[45] Date of Patent: Mar. 15, 1988

[54] PATIENT-OPERATED GLUCOSE MONITOR AND DIABETES MANAGEMENT SYSTEM

[75] Inventor: Lyle M. Allen, III, Durham, N.C.

[73] Assignee: Healthware Corporation, Durham, N.C.

[21] Appl. No.: 864,506

[22] Filed: May 19, 1986

[51] Int. Cl.$^4$ ............................................. G06F 15/42
[52] U.S. Cl. ....................................... 364/416; 422/55; 128/630
[58] Field of Search ......................... 364/413, 415–417; 128/903, 904, DIG. 12–DIG. 13, 665, 630, 632, 637; 356/445–446, 448, 244, 39; 436/14, 164

[56] References Cited

U.S. PATENT DOCUMENTS

| | | | |
|---|---|---|---|
| 3,996,928 | 12/1976 | Marx | 128/671 |
| 4,308,866 | 1/1982 | Jelliffe et al. | 364/413 X |
| 4,407,959 | 1/1983 | Tsuji et al. | 435/288 |
| 4,420,564 | 4/1983 | Tsuji et al. | 435/288 |
| 4,552,458 | 11/1985 | Lowne | 422/55 |
| 4,559,037 | 12/1985 | Franetzki et al. | 609/891 X |

OTHER PUBLICATIONS

Richard S. Surwit, "An Automated Compliance Enhancement Program in the Treatment of Insulin Dependent Diabetes Mellitus," Proceedings of the Fourth Annual Meetings of the Society of Behavioral Medicine, Baltimore, Md., p. 12 (1983).
Roger S. Mazze et al, "Computer-Based Diabetes Management System: An Aid for Patient Self-Care, Clinicians, and Researchers," Diabetic Patient Management, vol. II, No. 3, pp. 25–30 (May/Jun. 1984).
A. Schiffrin et al, "Optimizing Conventional Insulin Therapy Using an Insulin Dosage Computer," Diabetes 33, Supp. 1, p. 39A (Jun. 1984).
BCMC Better Control Medical Computers, Inc., "Insulin Dosage Computer 41," Handbook and Brochure entitled Introducing a Breakthrough in Insulin Therapy (1983-4).
William P. Newman, "A Glucose Home Monitoring Data Base System on a Pocket Computer," Diabetes, vol. 32, Supp. 1.1, p. 65A (1983).
David Michaels et al, "A Memory-Glucose Reflectance Meter for Automatic Data Recording," Diabetes, vol. 33, Supp. 1.1, p. 130A (1984).
V. G. Kuykendall, "Information Management for Glucometer Reflectance Photometer with Memory," Diabetes, vol. 33, Supp. 1.1, p. 132A (1984).
G. H. A. Schulz, "A Computerized Program for Intensified SC Insulin Therapy by Diabetes Self-Adjustment," Diabetes, vol. 33, Supp. 1.1, p. 26A (1984).
Ames Division, Miles Laboratories, Inc., "News from . . . Ames R&D," (1984).
Sophie A. Gerber, "Computer Monitor Diabetes Patients, Teach Self Care," Computing Physician, vol. 2, No. 3, p. 8 (Mar. 1984).

Primary Examiner—Francis J. Jaworski

[57] ABSTRACT

A monitor system is provided which includes means for measuring blood glucose values and for generating glucose data signals, monitor means coupled to the measuring means and including means for inputting patient data, means for transmitting and receiving data to and from the monitor means, and computing means for receiving glucose data signal in connection with administration treatment for diabetes mellitus.

10 Claims, 28 Drawing Figures

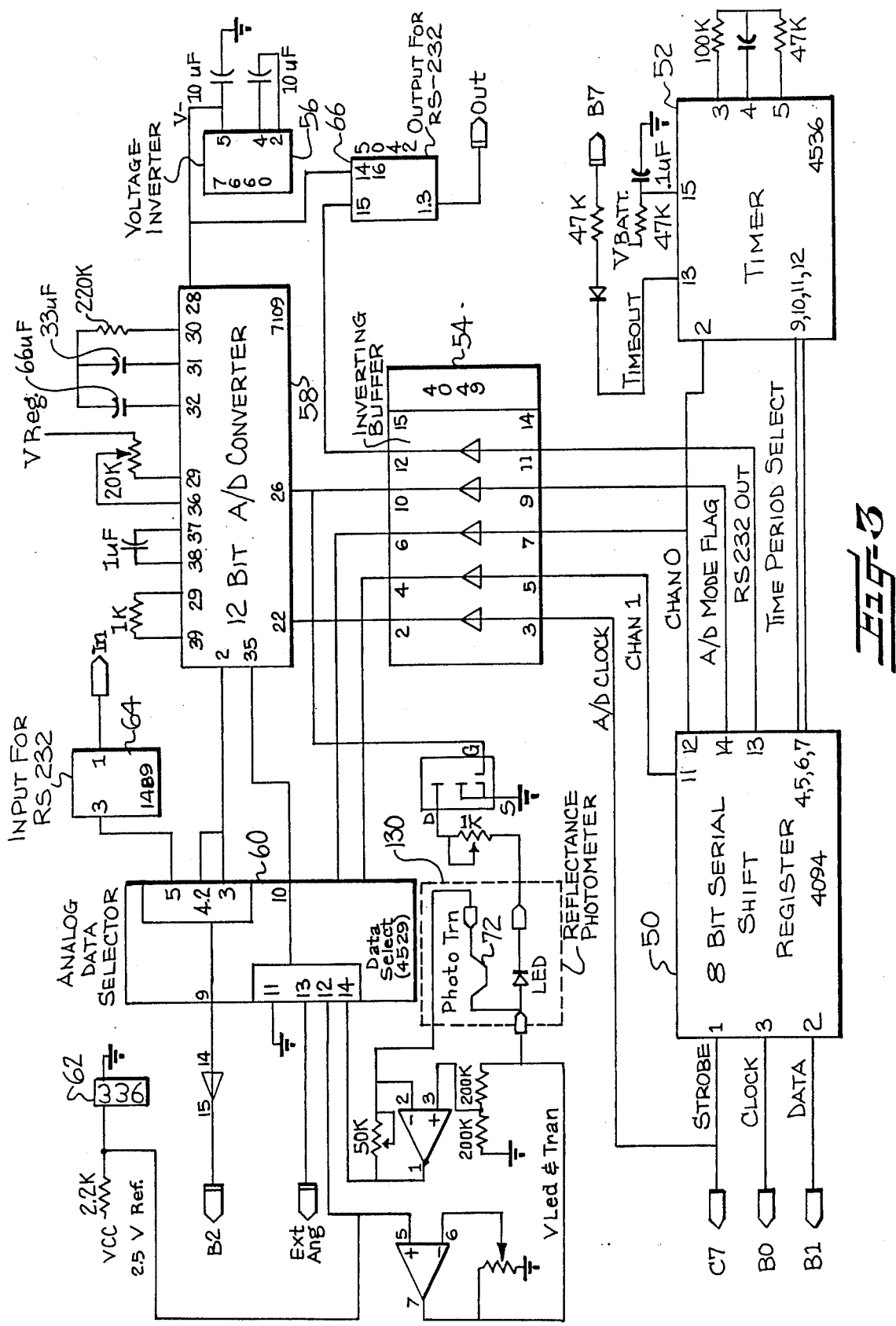

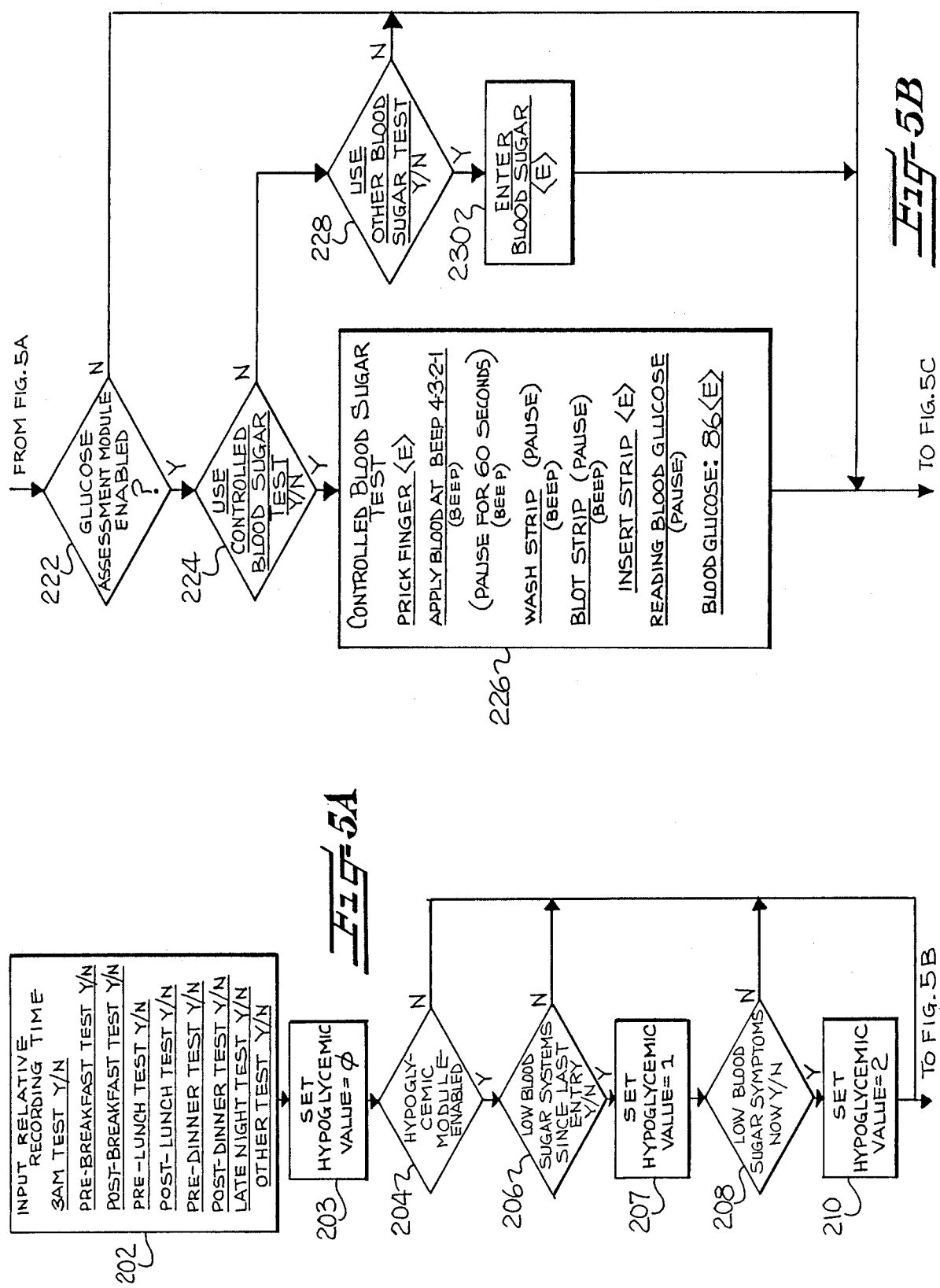

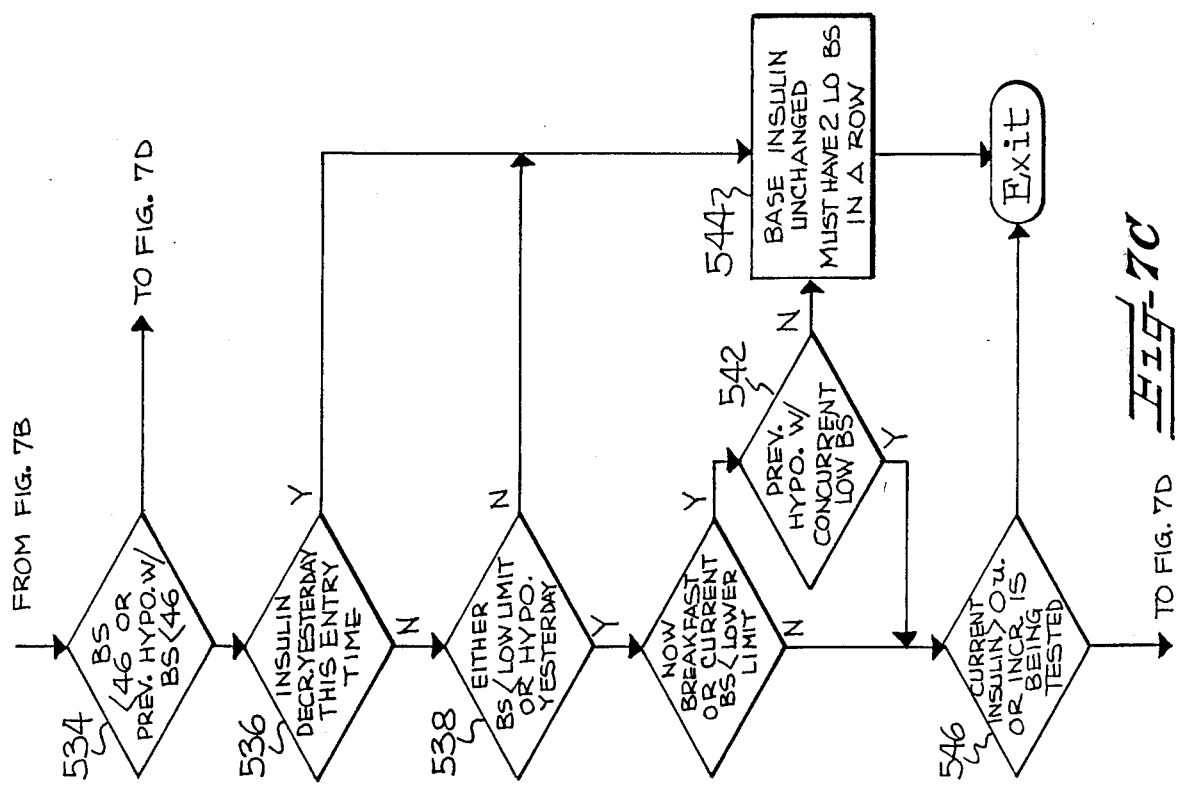
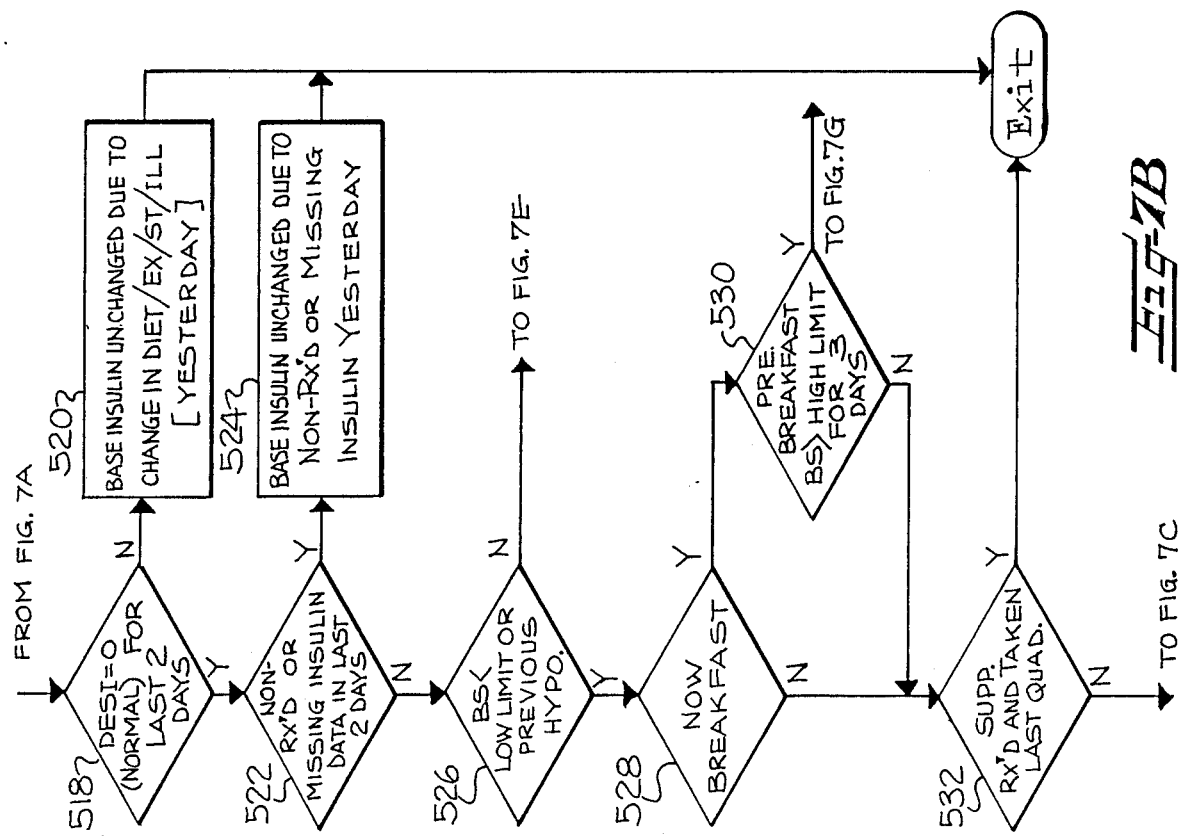

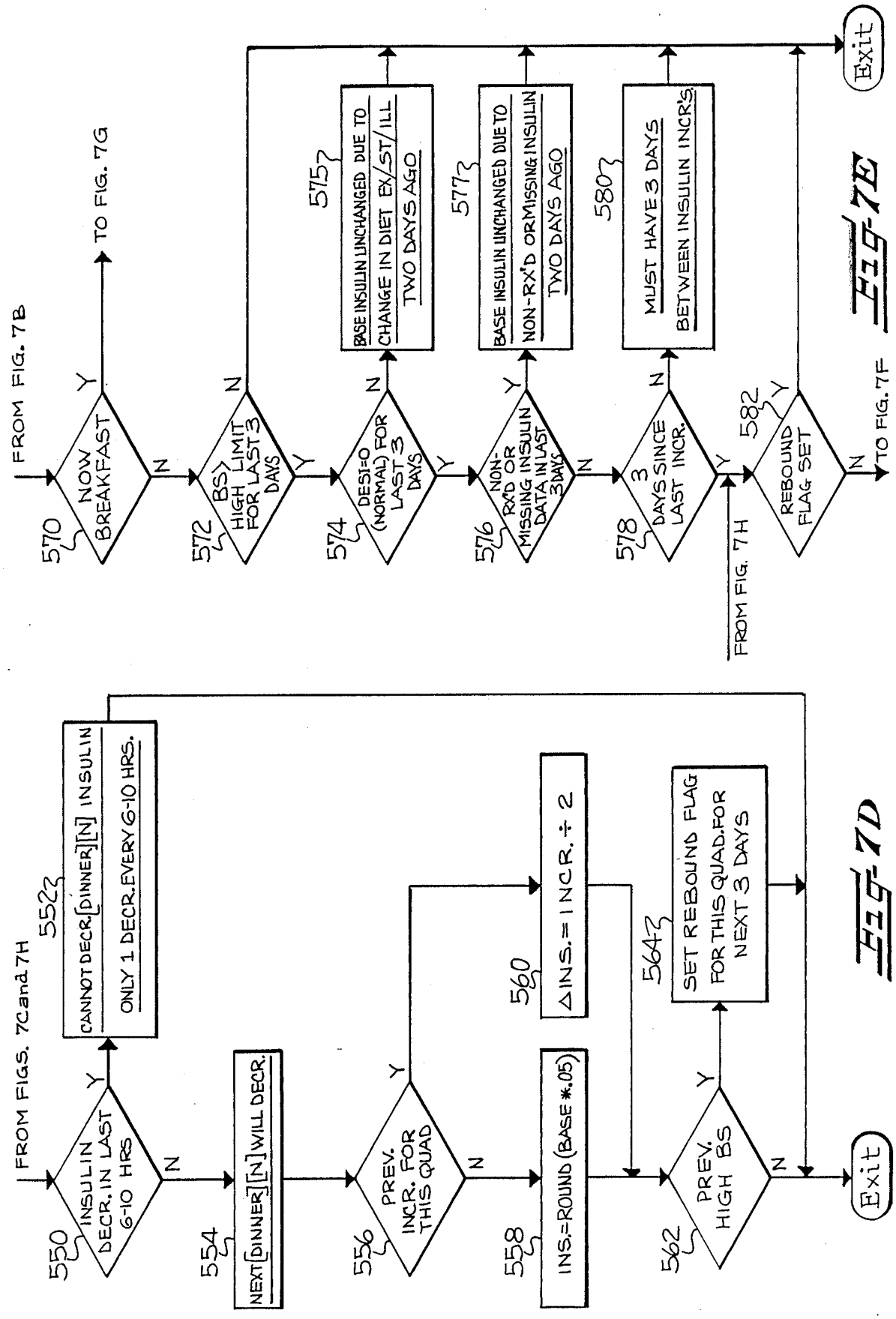

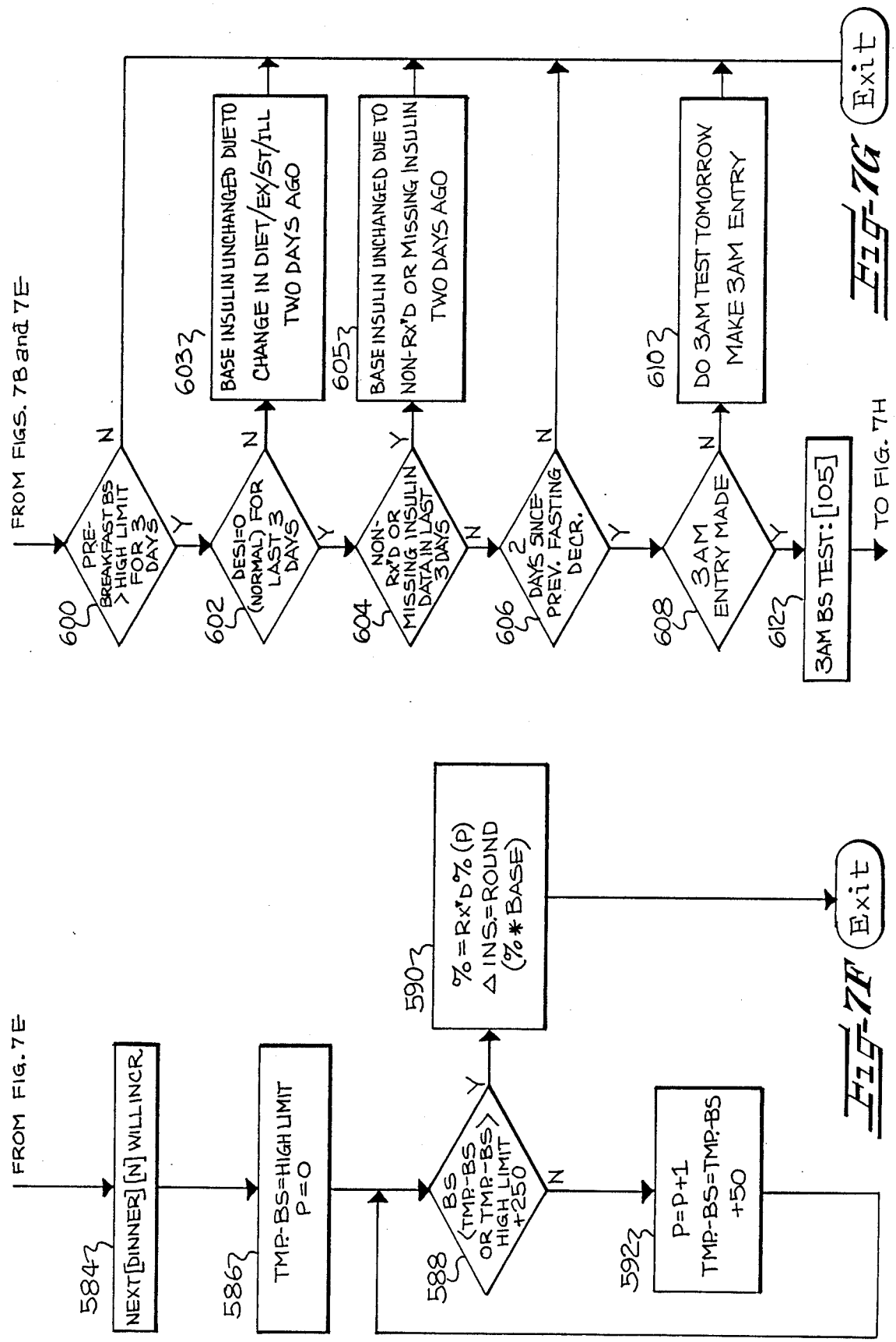

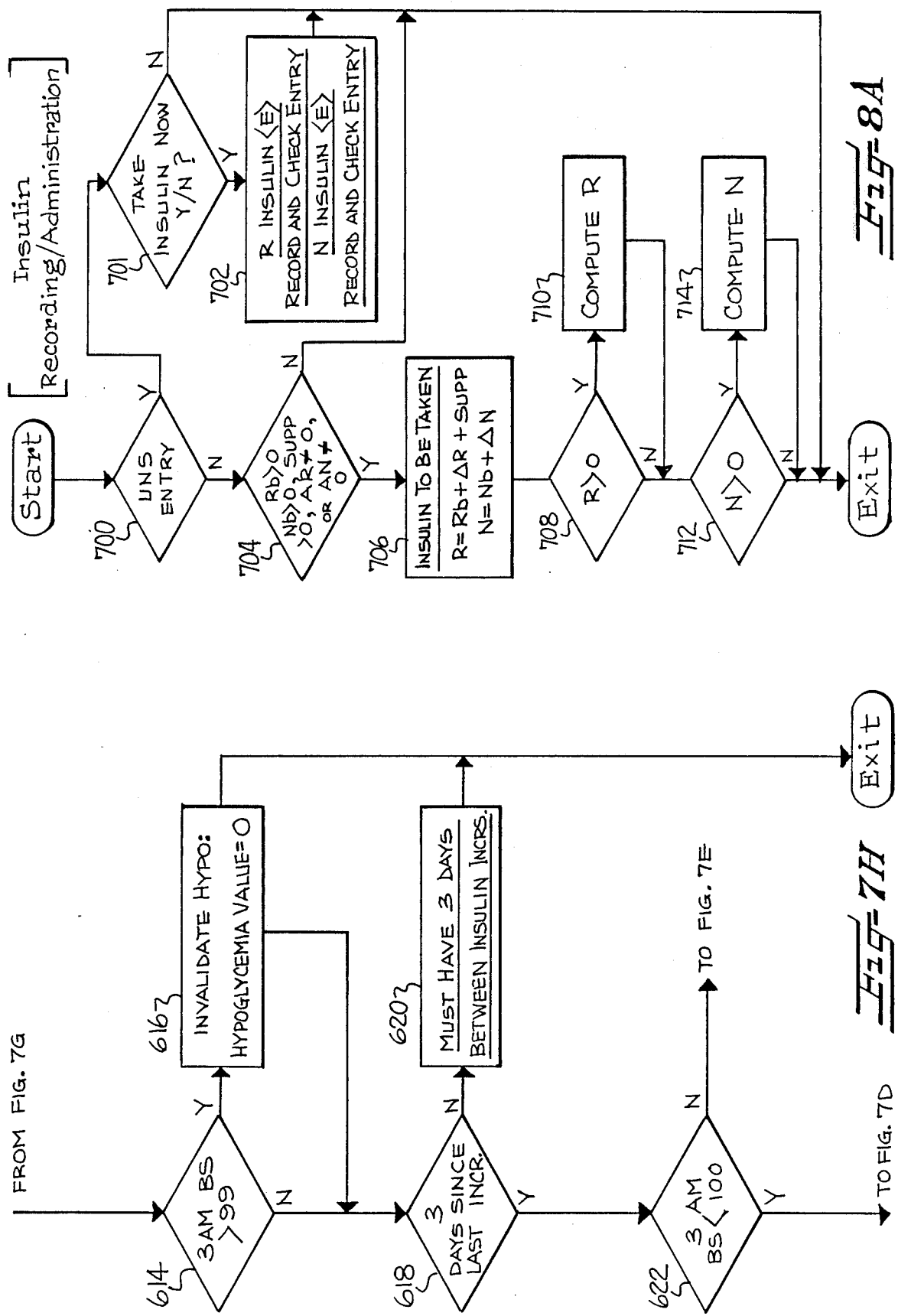

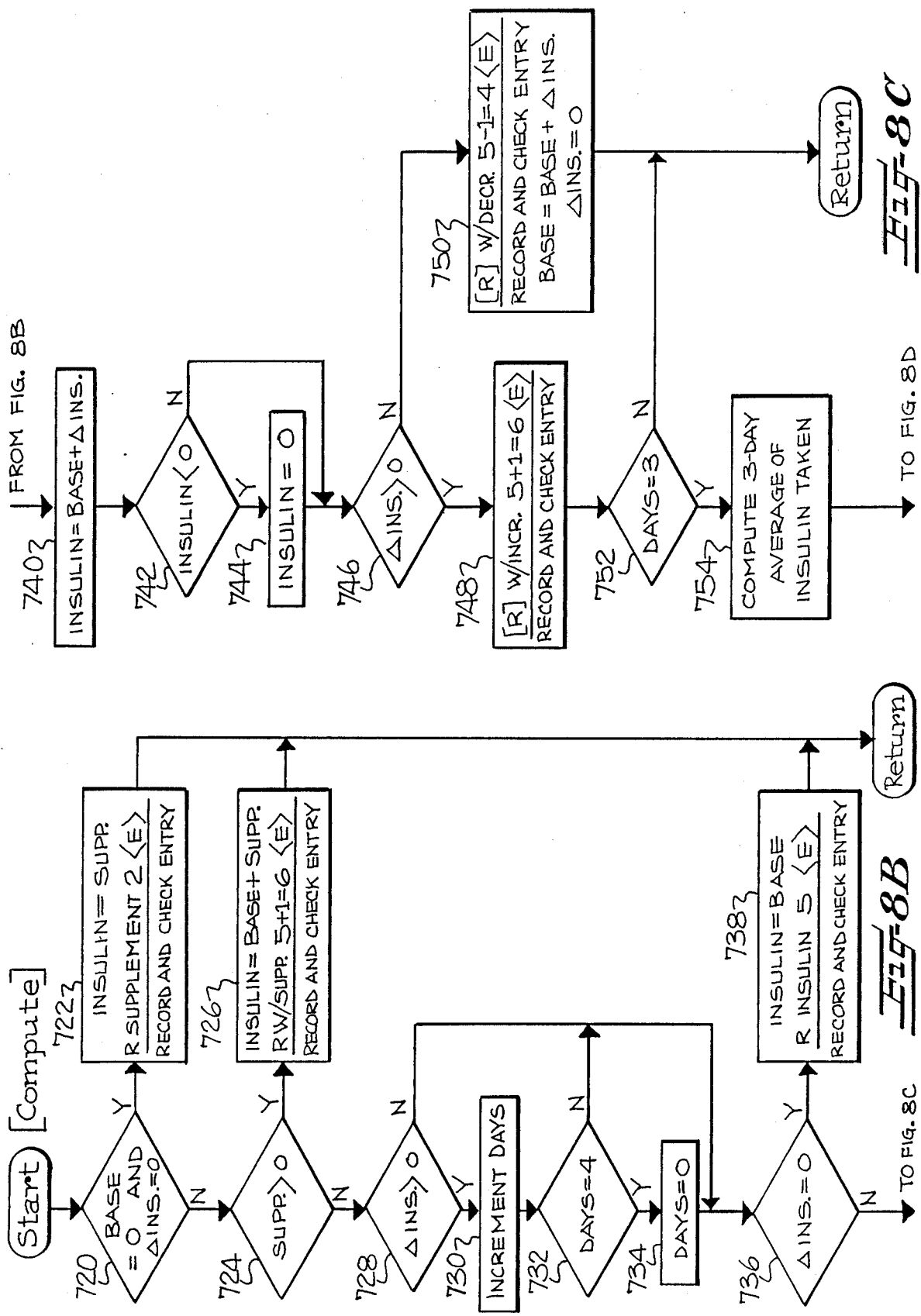

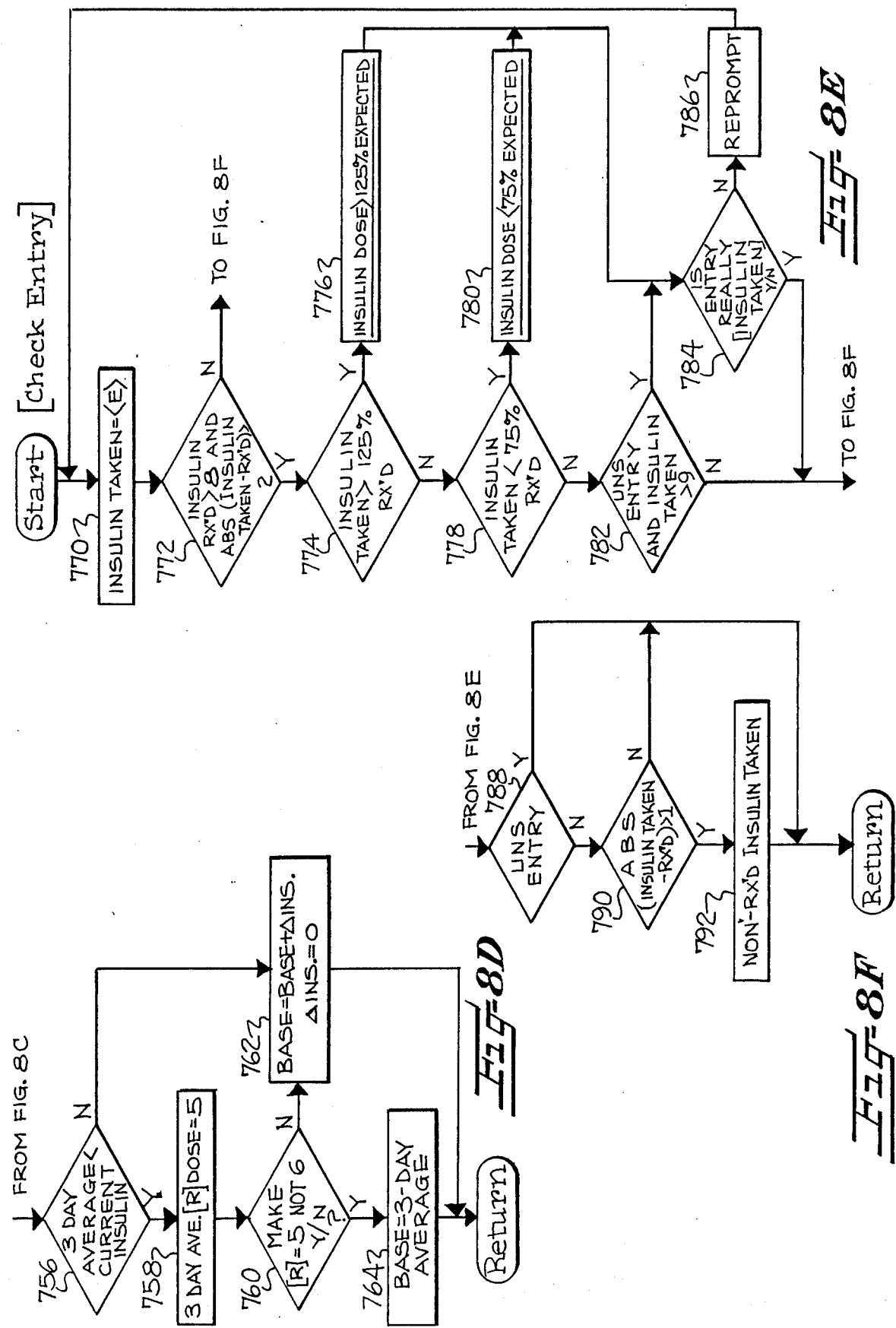

PATIENT-OPERATED GLUCOSE MONITOR AND DIABETES MANAGEMENT SYSTEM

BACKGROUND OF THE INVENTION

The present invention relates to a home monitoring system including a computer assisted reflectance photometer designed for measuring blood glucose values at home, and for storing and transmitting these and other data to a physician in connection with administration of treatment for diabetes mellitus.

In recent years there has been an enormous growth of monitoring blood glucose in the home. It has recently been estimated that 8% of the 5 million Americans currently diagnosed as suffering from diabetes mellitus monitor blood glucose at home.

Home glucose monitoring is an attempt to institute cybernetic control in the management of diabetes. In theory, patients monitor their blood glucose multiple times a day and record this information in log books. The information is then used by the patient's physician to periodically adjust the dosage of insulin or other therapeutic agent. Sometimes, the insulin-taking patient is given an algorithm to make insulin adjustments himself based on the data he collects.

In order for home glucose monitoring to impact significantly on the treatment of a given patient, one must assume that (1) the patient monitors home glucose as prescribed using correct techniques, (2) the patient records values reliably in a log book, (3) the patient comes to the physician's offices periodically to review his or her data, (4) the physician is able to make treatment recommendations based on viewing this data, and (5) the patient is in some cases able to adjust his or her own insulin based on this data.

These assumptions, however, frequently do not hold in practice patients often forget to monitor their glucose at the appropriate time; or, when they do they often use poor technique, making the values unreliable. Data may not be recorded properly in log books. Even when data is properly collected and recorded, most physicians cannot make intelligent treatment decisions by reviewing pages of raw data. Finally, insulin adjustment by the patient using data gathered from home glucose monitoring applied to an algorithm is a process too complicated for most patients to follow.

OBJECTS AND SUMMARY OF THE INVENTION

An object of the present invention is to provide an apparatus for accurately recording blood glucose data and other relevant treatment values.

Another object of the invention is to provide an apparatus for processing patient glucose data values in terms of a physician-prescribed algorithm.

An additional object is the provision of apparatus for transferring a patient's blood glucose data values over a communications channel to a physician's base computer station.

A further object of the invention is to provide a simpler, more reliable blood glucose monitoring system.

According to the present invention, as embodied and broadly described herein, a monitor is provided comprising, in combination, a reflectance photometer for measuring blood glucose levels, a circuit coupled to the reflectance photometer for converting the output from the reflectance photometer to a glucose data signal, and monitor means coupled to the circuit for storing the glucose data signal. The present invention also provides as part of the monitor means apparatus for inputting administered insulin data and means for comparing glucose data with the administered insulin data, and other data (stress, exercise, dietary intake) and outputting a recommended insulin dose based on a physician-prescribed algorithm in response to the comparison. The circuit comprises an analog-to-digital converter coupled to the glucose reflectance photometer for generating the glucose data signal, and a data multiplexer coupled to the output of the analog-to-digital converter and having an output coupled to the monitor means, for controlling the transfer of signals between the analog-to-digital converter and the monitor means.

In accordance with another aspect of the invention there is provided a monitor system comprising means for measuring blood glucose levels and for generating glucose data signals in response to the measurements, and monitor means coupled to the measuring means and including first means for inputting patient data, and second means for inputting physician precription data. The monitor means stores and evaluates the glucose data signals, patient data and physician data, and generates at least one prescribed insulin dose value in response to evaluating the stored glucose data signals, patient data and physician data.

Pursuant to still another aspect of the invention there is provided a monitor system comprising means for measuring blood glucose levels and for generating glucose data signals in response to the measurements. The invention further includes monitor means coupled to the measuring means and including means for inputting patient data, means for transmitting and receiving data to and from the monitor means, means for storing physician prescription data, glucose data signals and the patient data, and means for generating at least one recommended prescribed insulin dose in response to evaluating the stored glucose data signals, patient data and physician data. Further, the system of the invention includes computing means for receiving glucose data signals and storing patient data from the monitor, for evaluating the data according to a physican-prescribed algorithm and adjusting a physician insulin prescription in response to the evaluation, and for transmitting the physician insulin prescription to the monitor.

Additional objects and advantages of the invention will be set forth in part in the description which follows, and in part will be apparent from the description, or may be learned by practice of the invention.

BRIEF DESCRIPTION OF THE DRAWINGS

The accompanying drawings, which are incorporated in and constitute a part of this specification, illustrate a preferred embodiment of the invention and, together with the description, serve to explain the principles of the invention.

FIG. 3 is a detailed schematic diagram of the elements connected to the I/O control circuit shown in FIG. 2.

FIG. 5A is a functional flow chart illustrating the hypoglycemic symptom assessment firmware module employed in the monitor apparatus.

FIG. 5B is a functional flow chart illustrating the blood glucose assessment firmware module.

FIGS. 7A-7H taken together, are a functional flow chart diagram of the base insulin adjustment firmware module.

FIGS. 8A-8F taken together, are a functional flow chart diagram of the insulin recording/administration firmware module. FIGS. 8B-8D in particular, illustrate a subfunction of the recording/administration module for computing the current insulin dose. FIGS. 8E-8F illustrate another subfunction of the recording/administration module for checking the patient's data entry of insulin taken.

DETAILED DESCRIPTION OF THE PREFERRED EMBODIMENT

Reference will now be made in detail to the present preferred embodiments of the invention, examples of which are illustrated in the accompanying drawings.

Figure 1:
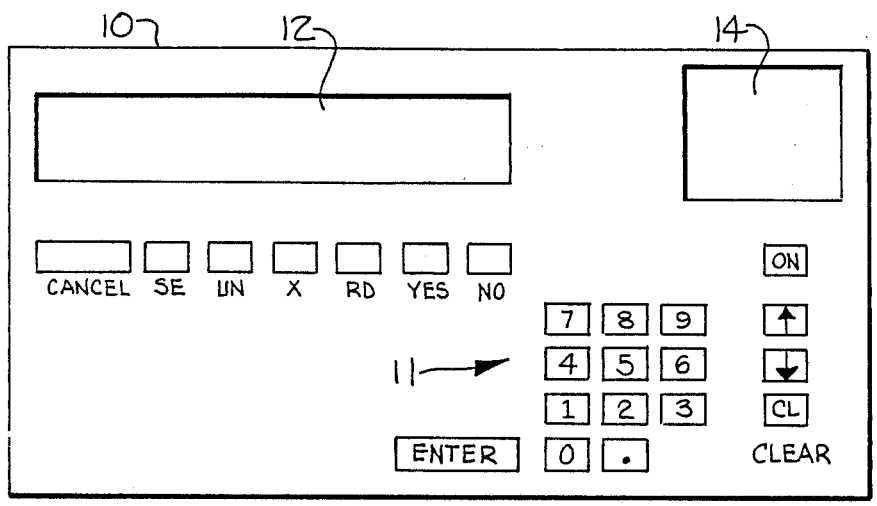
FIG. 1 depicts the monitor apparatus and illustrates its display, glucose reflectometer strip guide, and input key switches.

In FIG. 1 a monitor unit 10 is shown including a keyboard 11, a light emitting diode (LED) display 12 and a glucose reflectometer strip guide 14. The keyboard has a plurality of keys as follows. The "ON" key is pressed to turn the monitor on. The "SE" key (Schedule entry) is pressed to begin performing a scheduled blood test and/or insulin injection and to log behavioral data. "UN" (UNscheouled entry) is pressed to begin performing an unscheduled or "extra" blood test or insulin injection. "RD" (Review Data) is pressed to look at data from previous blood tests or insulin injections. After each blood test, the monitor will automatically provide the previous 3-day blood sugar average for the relative time of day. If desired, the actual numbers for each day can be displayed using the RD key. The "X" (special functions) key controls transmission of data, changing the speed of the display, changing the monitor clock, and changing the monitor alarm. The "CANCEL" key is pressed whenever a data entry error is made so that the monitor is returned to the beginning of a procedure to allow reentry of data.

Number keys 0, 1, 2, 3, etc., are used to enter information into the monitor, for example, weight, dietary intake, etc. The ENTER key is used after operation of a series of number keys and functions to enter the data into the system. ENTER also indicates "proceed to the next step." ENTER is used only when entering numbers to record weight, blood sugar, calories, food exchanges, doctor appointment dates, insulin doses or other medications. Whenever <E> appears on the display screen of the monitor, the ENTER key must be pressed following the numbers. The ENTER key is not needed when recording data relating to exercise, emotional stress, urine ketone levels or food intake, which all use a "1-5" scale.

At times the monitor will sequence a patient through a task, such as performing a finger prick, or will pause for the patient to think about the information which is displayed on a monitor screen. When the patient has finished a particular procedure, or the patient is ready to proceed to the next step, the patient must press the ENTER key to signal the monitor the patient is ready. Whenever the patient sees the 21 E> on the display screen, the patient must press the ENTER key to proceed.

"CLEAR" is pressed to clear the numbers which have been entered incorrectly, but before the ENTER key has been pressed. This allows a correction if the wrong numbers have been pressed for such items as weight, blood sugar, calories or insulin dose. This key cannot be used after pressing a number for exercise, emotional stress, food intake, or any item measured with a "1-5" or other menu type scale. The upwards arrow ($\uparrow$) and downwards arrow ($\downarrow$) keys indicate upward and downward movement of the display. These keys are used to display previous sequences of blood glucose tests or insulin injections.

The "YES" and "NO" keys are pressed in response to a prompt on the LED display requiring a yes or no answer.

Figure 2:
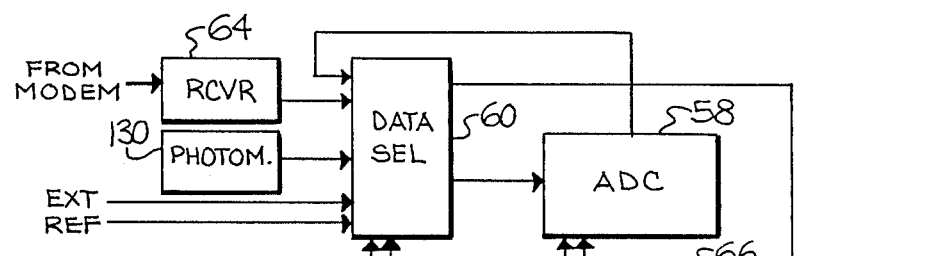
FIG. 2 is a system-level schematic diagram illustrating the monitor system of the invention.

Referring to FIG. 2, an illustrative embodiment of the monitor system 10 is described. In the exemplary arrangement illustrated, a reflectance photometer 130 is provided for obtaining blood glucose values. The analog output of the photometer is digitized by an analog to digital converter (ADC) 58 and fed into the system through a data selector 60.

The system also employs a timer 52 and a modem-coupled I/O port including a receiver 64 and an output driver 66. Timer 52 is controlled to give patient alarm signals, in a manner described subsequently and the receiver 64 and driver 66 provide an I/O port for inputting physician data and for coupling monitor data to a physician's operating system via, for example, a telephone communication channel.

Monitor 10 includes a microprocessor (MPU) 150 for providing necessary data storage, calculating and control functions. The system includes an input/output controller section 150a and a data bus 156 for channelling data to and from the MPU. Data selector 60 and a shift register 50 are used for coupling the ADC 58, timer 52 and the modem I/O port to the MPU. The keyboard unit 11, display unit 12, a random access memory (RAM) 152 and a read only memory (ROM) 154 are interfaced to the MPU through the data bus 156. An audio output unit 13 is also connected to bus 156 and is operated to provide "beep" signals to the patient during certain operations, as described hereinafter.

The monitor may utilize, for example, a Sharp model PC 1500A microprocessor system which has been modified by the addition of the elements shown above I/O controller 150a in FIG. 2 and more particularly illustrated in FIG. 3.

The reflectance photometer 130 operates to allow the patient to obtain accurate blood glucose readings simply and without physician assistance. The patient smears a blood sample (obtained, for example, by pricking a finger) on a conventional blood glucose test strip. After drying the strip for a predetermined time, the patient inserts the strip in the strip guide 14 (Fig. 1) and the system automatically reads the strip and enters a blood glucose value into the system in a manner described subsequently.

A schematic diagram of the hardware for obtaining blood glucose readings is shown in FIG. 3. Analog data selector 60 is coupled to the analog-to-digital converter 58, which may be a 12-bit unit identified by the "7109" model designation. Analog data selector 60 is coupled through inverting buffer 54 to the input pin 2 of timer 52. 8-bit shift register/latch 50 is coupled to timer 52 and through inverting buffer 54 to analog data selector 60 and A/D converter 58. Additionally, the RS 232 receiver 64 is coupled to receive an input from a telephone modem (not shown) and to feed the modem signal into the system via data selector 60. R5232 driver circuit 66 is coupled to transmit RS-232 compatible output signals to the telephone modem from the monitor system. Driver 66 is also coupled to buffer 54 to receive RS 232 outputs from shift register 50. A reference voltage generator 62 is coupled to analog data selector 60 and to the optical circuit of the reflectance photometer to provide a precision voltage reference thereto.

The reflectance photometer 130 operates to provide accurate blood glucose readings through the use of a light emitting diode and a phototransistor 72. The patient smears a blood sample (obtained, for example, by pricking a finger) on a conventional blood glucose test strip and follows a sequence of computer-generated prompts displayed on display 12. After drying the strip for a predetermined time, the patient inserts the strip in the strip guide 14 (FIG. 1) and the system automatically reads the strip and enters a blood glucose value into the system in a manner described subsequently.

The analog data selector 60 is a type-4529 LSI semiconductor chip. It controls the application of inputs to and the transmission of outputs from the A/D converter 58. Photometer output voltages produced by phototransistor 72, which reads the test strip, are coupled through amplifier 73 to input pin 14 of selector 60. Selection inputs applied to pins 6 and 7 from the channel 0 and channel 1 outputs of shift register 50 cause the signal on data selector pin 14 to be connected to output pin 10, whereupon the photometer signal is applied to input pin 35 of the A/D converter. The A/D converter is a type 7109 chip that digitizes the voltage at pin 35 under the control of the MPU 150. The latter provides a sequence of clock pulses at input C7 (FIG. 3, lower left) which is applied through buffer 54 to A/D clocking input pin 22. The A/D converter issues a status pulse at its output pin 2 after a number of clocking inputs. The status signal is transmitted to the MPU via pin 9 of the data selector 60. The number of clocks which are required to generate the status output is representative of the level of the analog input. The MPU 150 therefore calculates a digital photometer reading by transmitting clocking inputs to the A/D converter and monitoring the A/D status output while counting the number of applied clocking inputs.

The 12-bit analog-to-digital converter provides exceedingly precise measurements of output voltages from the glucose reflectometer circuit. Most monitors used for reading blood glucose levels are 8-bit systems and their peripheral chips are also 8-bit devices. However, the system of the present invention uses the 12-bit analog-to-digital converter chip's internal clock to measure the time of discharge after a single sample is converted. Since the rate of discharge is linear and constant, the system derives through software control a highly accurate reading using this technique. The MPU stores the digitized blood glucose reading under control of firmware in a manner more fully described subsequently.

Timer 52 is used under control of the MPU 150 to provide timed alarms in the form of "beeps" to signal the patient that various operations must be performed. The MPU enters data in parallel to inputs 9-12 of timer 52. This is done by feeding data through shift register 50 and applying it from output pins 4-7 of the latter to the timer inputs. The data thus entered sets a time value into the timer and "Channel O" signal from shift register output 12 subsequently initiates operation of the timer. Upon timeout of the timed interval timer 52 sends a signal to the MPU I/O control terminal B7, whereupon MPU takes the appropriate action, such as producing a "beep" sound through audio unit 13 and triggering a prescribed software routine to give the patient the necessary prompts, etc.

The monitor system can be used with a communications modem to communicate with a physician's base station over a telephone line. A modem coupled to the telephone line supplies inputs to receiver 64, which is a type-1489 chip implementing the "RS 232" communication protocol. Received data is channeled to MPU 150 via the data selector 60, which connects the signals applied to its input pin 5 to MPU input B2 via output pin 9. MPU generated data supplied on input B1 (FIG. 3, lower left) to shift register 50 is transmitted from shift register output pin 13 and sent to the modem via buffer 54 and RS-232 output driver 66, whereupon the data is placed on the telephone line.

Figure 4:
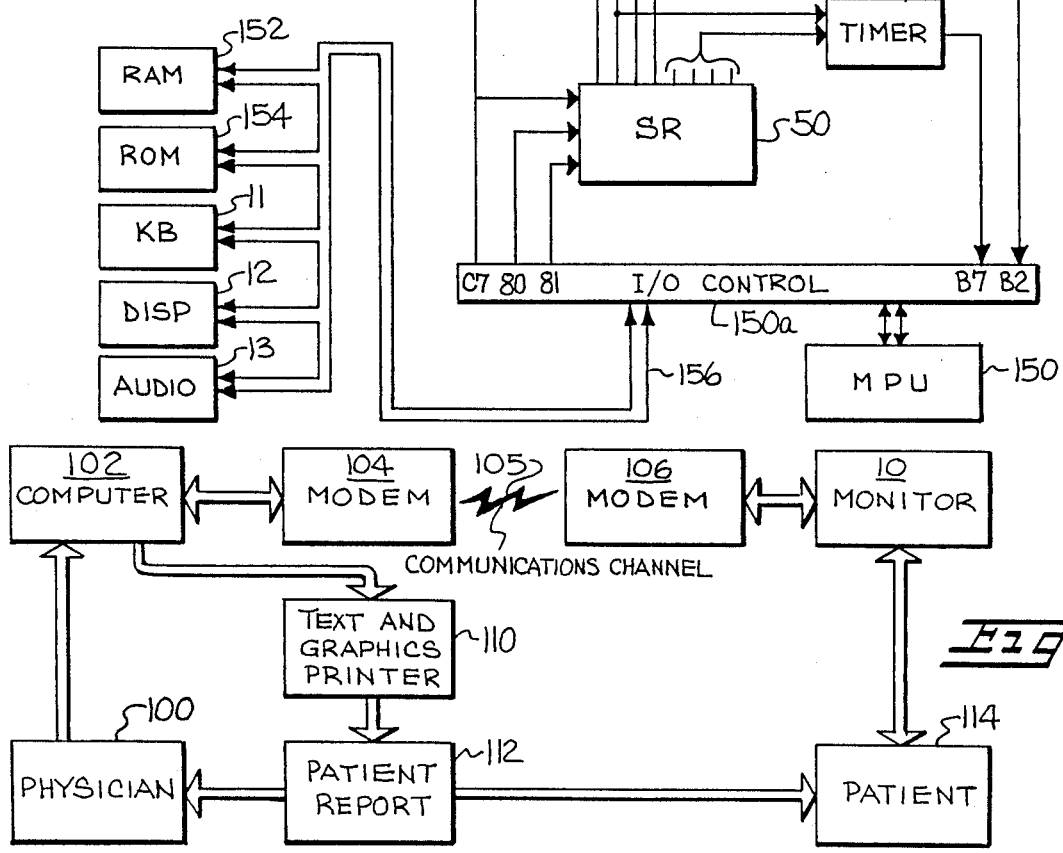
FIG. 4 is a system level diagram illustrating the physician/patient relationship based on use of a monitor system employing a modem for communicating with a physician base station.

As shown in FIG. 4, a physician base computer 102 is coupled to a modem 104 amd tp a text and graphics printer 110. Physician's computer 102 implements an algorithm for evaluating glucose and patient data from the monitor system 10. The data is evaluated according to the prescribed algorithm, and the patient's insulin prescription may be adjusted in response to the evaluation and transmitted to the monitor 10 via the modem link.

The monitor 10, operating independently of the modem link allows a patient 114 to use and evaluate glucose, insulin and behavioral data on a daily basis. Accumulated patient data is communicated to the physician's computer 102 through the modem link and computer 102 evaluates the data to produce a patient relink port 112 using text and graphics printer 110. The report presents a complete display of the analysis of the data received from the patient 114 via the monitor 10. The physician 100 interprets the report results and depending on his analysis, may revise assessment parameters, dietary, and/or insulin prescriptions.

The physician may then reprogram the monitor system by changing the assessment parameters or dietary, insulin, or other prescription stored within the monitor. This can be done by data inputs applied to the monitor directly at the physician base station or remotely over the modem channel.

In accordance with the embodiment shown, the monitor system includes key switches (shown in FIG. 1) for the patient to enter data indicating whether he is making a scheduled entry, an unscheduled entry, special functions or reviewing the data, and a number pad for a patient 114 to enter data. In exercising such a program option, when a patient 114 is making a scheduled entry, of which he would make up to eight scheduled entries per day, the patient depresses the scheduled entry key switch SE. Broadly, this option of the monitor system allows the patient to enter and record data according to physician prescribed assessment parameters. These may include the display of a prescribed basal insulin dose, recording insulin doses administered, base insulin dosage adjustment, supplementation of insulin doses to be prescribed, blood glucose, urine ketones or acetones, assessment of exercise and emotional stress, and assessment of body weight and dietary information. For an unscheduled entry, the patient 114 optionally records blood glucose and/or insulin taken during an unscheduled time period.

The use of the monitor system typically includes the operation of testing for a blood sugar level. The patient may perform the blood sugar test either as part of a Scheduled Entry or as part of an Unscheduled Entry. To perform the blood sugar testing routine, the patient must have the monitor system 10, a lancet device, a bottle of "Dextrostix" strips (or similar type of reagent strips), a wash bottle with water and blotting paper. Typically the patient will assemble the lancet device and then wash his hand in warm, soapy water. The patient then removes one Dextrostix strip from the bottle. The monitor system is turned on by pressing the ON key. Subsequently, either the SE or the UN key is depressed. After a sequence of preliminary prompts, the blood suger test is intitiated when the monitor displays "PRICK FINGER <E>." This signals the patient to prick the finger with the lancet device and obtain a drop of blood. After the drop of blood is obtained, the patient picks up the test strip with, his free hand and presses the ENTER key.

The monitor system proceeds to prompt, "APPLY BLOOD AT BEEP." In four seconds the monitor produces a "beep" from its audio unit 13, which is the patient's signal to apply the blood onto the pad of the test strip. The monitor system then counts down 60 second intervals.

After 60 seconds, the monitor again beeps and displays the prompt, "WASH STRIP." This is the signal to rinse the blood off the strip, using a thorough, even wash for about 2–3 seconds. The monitor then beeps and prompts the patient, "BLOT STRIP." The patient at this point will blot the test strip onto a paper towel twice. Another beep is generated by the monitor system and the prompt "INSERT STRIP <E>" is displayed. This is a signal for the patient to insert the strip into the glucose reflectometer strip guide 14. When the strip is properly inserted, the patient presses the ENTER key switch.

The monitor system pauses for a few seconds, while it displays "READING BLOOD GLUCOSE." During this time, the monitor system is determining the blood glucose sugar value by reading the color of the test strip using reflectance photometer 130. Subsequently, the monitor displays "BLOOD SUGAR: [value] <E>." The monitor automatically stores the blood sugar value into its memory 152, eliminating erroneous or deliberately misleading recordings common with pencil and paper methods. After the patient has seen the blood sugar value displayed, the patient is ready to proceed to the next assessment module, and presses the ENTER key switch. This completes the internal blood sugar test.

The reagent strips used with the monitor systems are capable of measuring blood sugar level because the pad on the strip contains chemicals which detect and react with glucose. When a drop of blood is placed onto the pad, the glucose in the blood starts to react with the chemicals in the pad. The pad begins to develop a blue color. A low blood sugar produces a light blue color, a high blood sugar produces a dark blue color.

When using the "Destrostix" type of reagent strip, the blood must remain on the pad for exactly 60 seconds for the pad to develop the correct color to indicate the level of blood sugar. If a person's eyes were very sensitive to color shades, the person could determine his blood sugar by comparing the color of the pad with a special color chart, such as the one on the side of the "Dextrostix" bottle. If the person examines this color chart, the person would realize that the shades "look a lot alike" and only six blood sugar levels are listed.

The monitor system 10 employs a special optical system, the glucose reflectance photometer 130, previously described in connection with FIG. 3, for distinguishing a large number of color shades. Each shade of blue or other color corresponds to a certain blood sugar level. The monitor 10 can be programmed so that other types of reagent strips can be used. In such a case an adjustment in the A/D converter control software would also be required to provide correct conversion values.

The results of the blood test are displayed as a number. This number indicates the amount of glucose per unit of blood in milligrams per deciliter, abbreviated as "mg/dl."

When a patient works with a physician, the patient and physician usually have agreed upon certain times that the patient will routinely perfOrm a blood test and/or take an insulin shot. The monitor 10 is programmed to know when a patient is scheduled to perform a blood test or to take an insulin shot. This information is entered into the computer memory 152 as prescribed by the physician. Usually the scheduled time is not an exact time, but is a time relative to a meal, such as before or after breakfast, before or after lunch, before or after dinner or at bedtime. A "Scheduled Entry" is an entry performed when the patient does a blood test or takes a shot of insulin at a prescribed and expected time, relative to the appropriate meal. There may be times however that the patient performs an extra blood test, or takes an extra shot of insulin. For example, the patient may desire to check to see if his blood sugar is low or perhaps an infection has caused the patient's sugar to rise, suggesting the need for an extra shot of insulin. Whenever these situations occur, they give rise to an "Unscheduled Entry."

Each time the patient performs a scheduled entry, the monitor asks the patient about previous insulin reactions, exercise, emotional stress, illness, weight and dietary intake. Each of these factors may change the patient's blood sugar.

In recording insulin reactions, the monitor system prompts the patient to enter information about recent insulin reactions, by asking "LOW BLOOD SUGAR SYMPTOMS SINCE LAST ENTRY—Y/N?" If a patient has not had symptoms of low blood sugar since the last scheduled entry and the patient does not feel he is having a reaction now, the patient enters NO to give a no answer. If the patient has had symptoms of low blood sugar since the last scheduled entry or if the patient feels these symptoms now, the patient enters YES to give a yes answer. The monitor system then asks the patient when he had those symptoms, by displaying, "LOW BLOOD SUGAR SYMTOMS NOW—Y/N?" In response to this prompt, the patient presses NO if the patient does not feel he is having symptoms of low blood sugar now and YES if one feels he is having symptoms of low blood sugar.

In recording exercise, the monitor prompts the patient for information about activity, by asking, "EXERCISE (1-5)?" The patient will then enter the measurement of exercise or activity since the last scheduled pre-meal entry, using the following scale:

1=substantially less exercise than usual for this time of day.
2=somewhat less exercise than usual for this time of day.
3=usual amount of and type of exercise for this time of day.
4=somewhat more exercise than usual for this time of day.
5=substantially more exercise than usual for this time of day.

Note that the patient is being asked how active he has been compared with his usual amount of activity for the period of time since the last scheduled entry. For example, while the patient sleeps the patient does not exercise. The next morning, for a pre-breakfast entry, this would be entered as a "3", if the patient actually slept through the night. However, if for some reason the patient were awake half the night pacing about the house, for the pre-breakfast entry the patient would enter a "4" as a rating of the patient's night exercise.

Likewise, if the patient usually runs five miles every afternoon the patient would enter a "3" for the pre-dinner exercise entry on days that the patient runs five miles. However, if the patient were unable to run one afternoon because the patient had to work late, the patient might enter a "1" for his predinner exercise entry.

In recording emotional stress, the monitor system prompts the patient to enter information about emotional stress by asking "EMOTIONAL STRESS (1-5)?" In response, the patient enters the measurement of emotional stress the patient has felt since the last scheduled entry, using the following scales:

1=substantially less stress than usual for this time of day.
2=somewhat less stress than usual for this time of day.
3=usual amount and type of stress for this time of day.
4=somewhat more stress than usual for this time of day.
5=substantially more stress than usual for this time of day.

In recording illness, the monitor system prompts the patient to enter information about illness by asking "ARE YOU SICK—Y/N?" The patient presses NO if he has not felt sick since the last scheduled entry, ending the assessment of illness. If the patient presses YES, the monitor system displays, "HAVE A FEVER—Y/N?" The patient responds by pressing YES or NO.

If the physician desires the patient to keep track of body weight, the monitor prompts the patient each morning before breakfast with the question, "RECORD BODY WEIGHT—Y/N?" The patient will press either NO or YES, depending upon whether the patient weighed himself that morning. If the patient responds YES the monitor prompts, "ENTER WEIGHT <E>." The patient must then enter the weight value in pounds, followed by actuation of the ENTER key.

The monitor is able to collect dietary information in three different ways. The physician will specify which way the monitor should ask about food intake to reflect the way best suited for the individual patient based on his motivation and education in quantifying dietary intake. The first method uses a 1-5 scale to record dietary intake. If this method is chosen, the monitor system prompts, "FOOD INTAKE (1-5)?" The patient will then enter the number which best describes his food intake since the last scheduled entry:

1=none or almost no food for that meal or snack.
2=somewhat less than usual (but at least 75% of usual intake).
3=usual amount and type of food for that meal or snack.
4=somewhat more than usual (but less than 25% more than usual).
5=much more than usual.

The second method uses calorie counts to record dietary intake. If this method is chosen, the monitor system displays the prompt, "DIET [Calories]: <E>." The patient will then enter the number of calories the patient has eaten since the last scheduled entry.

The third method calls for an input of food exchange data.

The monitor system is capable of reviewing previous blood sugar values. This can be accomplished by the following procedure. First the patient turns the monitor on by pressing the ON key. Then the patient selects the review data option by pressing the RD key. The monitor displays the prompt, "REVIEW DATA." The display then tells the patient that the data will be presented with the most recent first. Then the display asks the patient to review the data one test at a time, "1-EACH", whether he wants to review the data one test at a time, 1-EACH", or one day at a time "2-BY DAY." In response, the patient presses "1" if he wishes to review each blood sugar test value and associated insulin administration record, one at a time. The patient presses "2" if he wishes to review the blood sugar values one day at a time, viewing premeal entries of blood sugar and insulin only.

If the patient presses "1", the most recent blood sugar and insulin levels are displayed along with the data concerning date, time, and types of insulin administered. For example the following information describes a breakfast scheduled entry:

Dt15 Brk B=111 R12 N$^{15}$

The date is the 15th of the month (Dt=date) and the recorded blood sugar was 111 mg/dl. The amount of R type of insulin taken was 12 units and the amount of N type insulin recorded was 15 units. Pressing the upward arrow key ( ↑ ) will continue to present the data moving backwards in time. By pressing the downward arrow key ( ↓ ), the data will be presented moving forward the displayed time. When one has seen all the data stored in the monitor, the display will read "END OF DATA, AGAIN—Y/N?" The patient will press YES if the patient wants to continue viewing the information, and will press NO if the patient does not. The patient may press the CANCEL key to interrupt the display whenever the patient no longer wants to look at the data. In response, the monitor system displays "CANCEL ENTRY--Y/N?" The patient presses YES and the monitor turns itself off.

If the patient chooses to review data under the "by day" option, the monitor displays two lines to let the patient know how the information will be presented. The first line indicates "PREMEAL BLD SUGAR BY DAY" the second line will indicate "FORMAT DAY BRK LUN DIN LtN." With this option the monitor displays only the scheduled blood sugar tests performed before meals (PREMEAL) and at bedtime (LtN—latenight). Unscheduled blood tests and those performed after a meal (2 hours post prandial) will not be displayed.

The blood sugar values will be displayed in the following order: pre-breakfast blood sugar, pre-lunch blood sugar, pre-dinner blood sugar, then bedtime blood sugar. The data from the most recent day will be displayed first. For example, Dt 19 112—143 95

This display tells the patient that on the 19th day of the month (Dt=date), his pre-breakfast blood sugar was 112 mg/dl. No blood sugar test is reported for the pre-lunch time, either because the patient did not do a test at that time or because the pre-lunch time is not a scheduled entry time for him. His pre-dinner blood sugar was 143 mg/dl, and his bedtime blood sugar was 95 mg/dl.

By pressing the upward arrow key to review the blood sugar values for the previous day, the data displayed on display screen 12 will move backward in time. Again, when the patient has seen all the data stored in the monitor, the display will read "END OF DATA, AGAIN—Y/N?" The patient presses YES if the patient wants to continue viewing the information and NO for not viewing the information. The patient may press the CANCEL key to interrupt the display whenever he no longer wants to look at the data. In response, the monitor displays "CANCEL ENTRY—Y/N?" When the patient presses YES the monitor turns itself off.

The monitor also implements several special functions. These special functions can be activated by first turning the monitor on by pressing the ON key and then by pressing the X key. The monitor then prompts the patient to select the function desired by entering an appropriate number:

| | |
|---|---|
| 1 - DS | Function to change the display speed. |
| 2 - BEEP | Function to change the monitor alarm. |
| 3 - XMIT | Function to transmit data to the diet care central computer over the telephone. |
| 4 - TIME | Function to change the current date/time information in the monitor. |
| 5 - DATA XFER | |
| 6 - HELP | |

The change speed function is activated by pressing the 1 key. The display indicates "THE DISPLAY NOW FLASHES (pause). THIS FAST—. Y/N?"" In the underlined blank, the system displays a number between 20 and 255, wherein 20 is the fastest speed and 255 is the slowest. In response to the patient depressing the NO button, the monitor system prompts the patient to enter the speed desired, by prompting "NEW SPEED (20-255):—<E>." The patient presses the appropriate number keys, then press the ENTER key.

The monitor then flashes the previously displayed two lines across the display at the new selected speed so that the patient can judge if the speed is too fast or too slow. These lines include:

THE DISPLAY NOW FLASHES (pause). THIS FAST—Y/N?

The processes is repeated until an appropriate speed has been selected.

If the patient selects special function no. 2 "BEEP", a majority of monitor alarms can be turned on and off. The monitor beeps at certain times to make the patient aware of problems or to signal the patient to perform a procedure. The system produces beep sounds through the operation of audio unit 13, which is controlled by the MPU 150 and timer 52 (FIGS. 2 and 3). This may occur as part of a blood sugar test routine, or the alarm may be signaling the patient that it is time to undertake a scheduled entry.

However, there may be times when the patient does not want to have the monitor make any sounds, perhaps when there are others around and the beeps may be distracting. The "BEEP" special function allows the patient to turn off many of the beeps. There are some beeps that cannot be turned off, however. If the monitor alarm is turned off, the only beeps that will remain are those which are needed to time certain procedures, such as applying or moving blood from a reagent strip during a blood sugar test. If the beeps are turned off, it is important that the patient watch the display screen carefully. The alarm system used to signal the patient to initiate a scheduled entry is enabled and set for various times by the patient's physician using computer 150.

The monitor system can additionally be used to transmit data by selecting special function no. 3 "XMIT." This function is used when it is time to connect the monitor to the telephone to transmit information to the central computer 150.

Typically, once a week a patient transmits (usually) in the evening the data that have been stored in the memory 152. When a patient is ready to transmit data, the patient must assemble the following equipment: the monitor, the modem, and a telephone cord to connect the modem to the phone rack. The modem is plugged into a wall outlet for electrical power. The modular adapter is attached to the telephone wall box and left in place. This allows the patient to use the modem without disconnecting the telephone, and at the same time, the adapter will not interfere with the normal function of the telephone. The use of MODEMS connected for data transmissions are well known in the art and their actual use as embodied herein is not further discussed.

In response to the patient pressing the 4 key to select the "TIME" special function, the patient can check and/or change date and time information. Upon entry into this module, for example, the following prompt is displayed:

TUES 1-1-86 14:53—Y/N?

If the patient confirms the current information is correct by pressing Y this module is exited. If the patient responds by pressing the NO key, then the following prompts appear for entry:

| | |
|---|---|
| Year? | <E> |
| Month? | <E> |
| Day? | <E> |
| Hour (0-23)? | <E> |
| Min? | <E> |

When completed, the newly entered date and time information is confirmed by the patient as indicated above.

The various functions of the monitor system are controlled by computer programs stored in the system's memory in either RAM 152 or ROM 154. Programs which are relatively non-changing are stored in the ROM module and are changed only by replacing the module in a system servicing environment. Programs stored in the RAM module are readily changeable by reading new program data into the system via the modem I/O port. Programs are referred to herein as "firmware" without regard to the particular memory module in which they reside.

FIG. 5A depicts the hypoglycemic symptom assessment program module. Referring to FIG. 5A, the patient specifies the time of day in step 202 by pressing YES or NO, on the monitor system keyboard 11 (FIG. 1) in response to the following sequence of firmware controlled prompts which appear on LED display 12:
3-AM TEST Y/N?
PRE-BREAKFAST Y/N?
POST-BREAKFAST Y/N?
PRE-LUNCH Y/N?
POST-LUNCH Y/N?
PRE-DINNER Y/N?
POST-DINNER Y/N?
LATE NIGHT Y/N?
OTHER TEST Y/N?

In response to the relative recording time input, the program in the monitor system then proceeds to the determination of hypoglycemic symptoms.

As shown in FIG. 5A, the hypoglycemic value is set to an initial value of "0" (step 203). A determination is then made in step 204 as to whether the hypoglycemic module has been pre-enabled by the physician. If the hypoglycemic program module 204 is not enabled, the program will proceed to the next program module.

In assessing the hypoglycemic symptoms, a determination is made as to whether low blood sugar symptoms have been exhibited since the last execution of the program module. The LED display 12 prompts the patient with, "LOW BLOOD SUGAR SYMPTOMS SINCE LAST ENTRY?—Y/N? " (step 206). In response to a NO input from the patient, the program proceeds to the next assessment program module. In response to a YES, the program module sets the hypoglycemic value equal to "1" (step 207) and then displays the prompt "LOW BLOOD SUGAR SYMPTOMS NOW?" (step 208). In response to the patient depressing NO, the program proceeds to the next assessment module. In response to a YES, the program module sets the hypoglycemic value equal to "2" (step 210) and proceeds to the next assessment module.

FIG. 5B shows a blood glucose assessment program module. A determination is made in step 222 as to whether the blood glucose assessment module has been enabled by the physician. If so, then the display 12 prompts the patient "USE CONTROLLED BLOOD SUGAR TEST Y/N?" (step 224). If patient responds YES, then in step 226 the patient is prompted through a series of carefully timed steps to accurately determine the patient's blood glucose level using the system's local photoreflectometer system. If the patient responds NO, then the monitor asks, "USE ANOTHER BLOOD SUGAR TEST Y/N?" (step 228). If the patient depresses NO, the program proceeds to the next assessment module. If the patient depresses YES the monitor prompts the patient to record the blood sugar value (step 230) derived from an external glucose assessment method. After the patient records a blood sugar value into the monitor the program proceeds to the next assessment module.

The controlled blood sugar test shown in step 226 is implemented as follows. The patient is initially prompted to prick a finger and subsequently to apply a blood smear to a standard chemically treated test strip at the end of a 4-second, beep-terminated countdown. The program module then proceeds through a 60-second countdown and sounds another beep. After this beep, the patient is prompted to wash the strip followed by a beep, then to blot the strip followed by a beep, and finally to insert the strip into the reflectometer strip guide 14. At this point, the program implements an A/D conversion cycle to obtain the blood glucose reading through operation of photometer 130 and A/D converter 58. The reading is displayed on display 12 and is stored in RAM 152 when the patient actuates the ENTER key. After entry of the reading, the program exits the blood glucose assessment module and proceeds to the next assessment module.

Figure 5D:
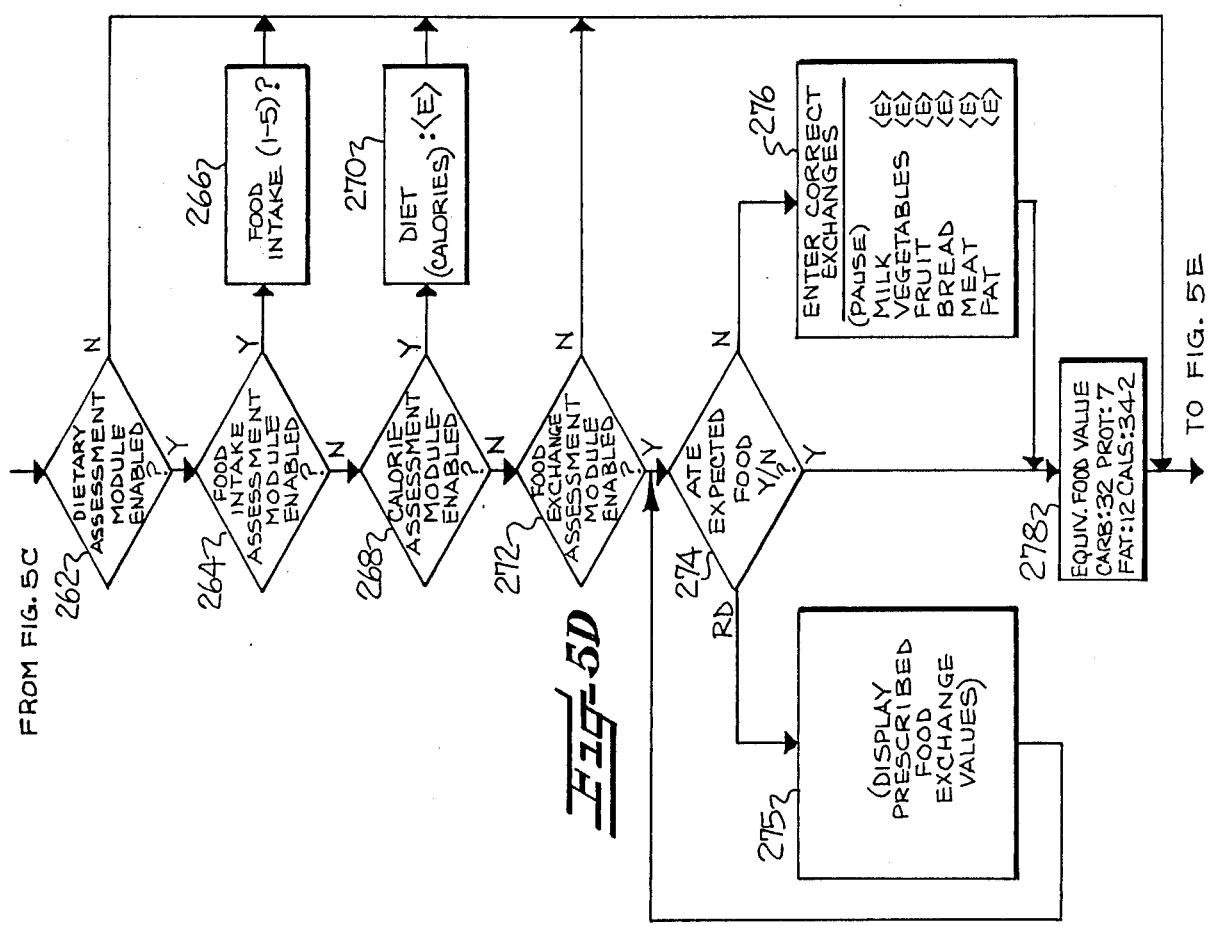
FIG. 5D is a functional flow chart illustrating the dietary assessment firmware module.
Figure 5C:
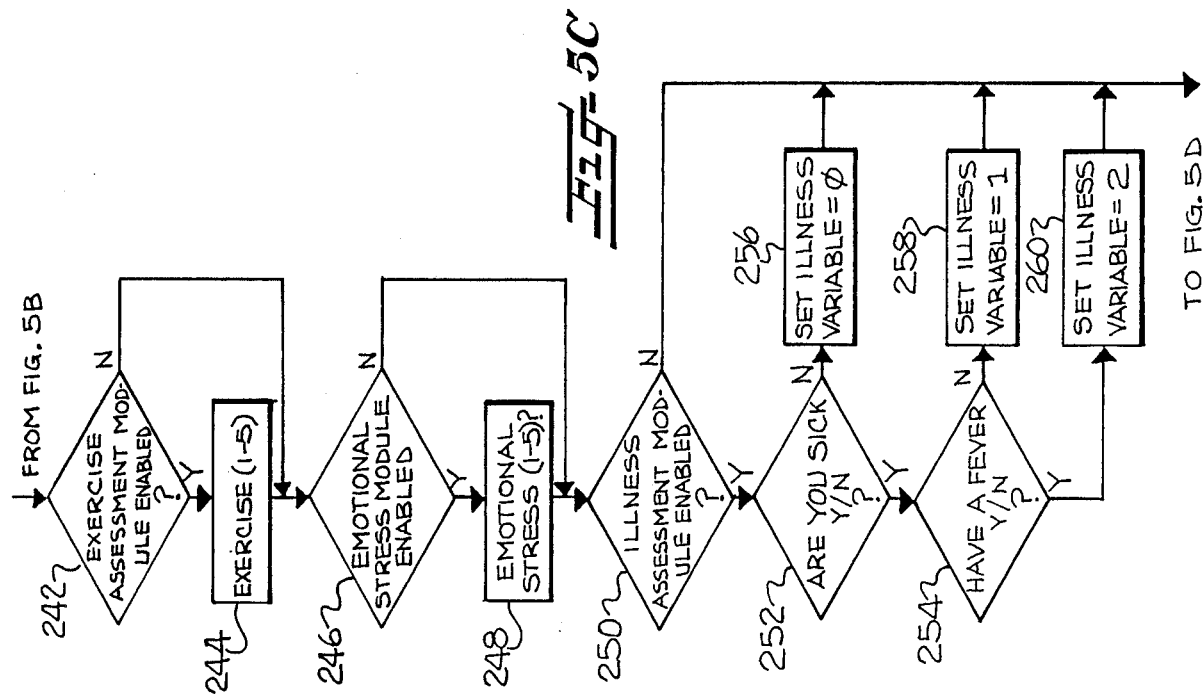
FIG. 5C is a functional flow chart illustrating the exercise assessment firmware module, emotional stress assessment firmware module, and illness assessment firmware module.

FIG. 5C illustrates the exercise assessment module, emotional stress assessment module, and illness assessment module. Initially a determination is made as to whether these assessment modules are enabled by the physician, for the relative time period selected by the patient for data recording. If an assessment module is not enabled the program proceeds to the next assessment module.

First a determination is made as to whether the exercise assessment module is enabled (step 242). If enabled, the program module prompts the patient (step 244) to enter an exercise value between the range of 1-5 by displaying "EXERCISE (1-5)?" In response to operation of one of the keys 1-5, the program proceeds to the next assessment module.

A determination is then made as to whether the emotional stress module is enabled (step 246). If enabled, the monitor prompts the patient (step 248) to enter an emotional stress value between the range of 1-5 by displaying "EMOTIONAL STRESS (1-5)?" In response to the patient's actuation of a key 1-5, the program proceeds to the next assessment module.

The illness assessment module is initiated after a determination is made as to whether the illness assessment module is enabled (step 250). The display 12 prompts the patient, "ARE YOU SICK—Y/N?" (step 252). If the patient responds that he is not sick by pressing NO, the program module sets the illness variable to "0" (step 256) and exits the module. If the patient enters a YES, the monitor displays the prompt "HAVE A FEVER Y/N?" (step 254). Upon entering a NO, the program module sets the illness variable to "1" (step 258) and proceeds to the next assessment module. If a YES is entered in response to the prompt in step 254, the program module, sets the illness variable to "2" (step 259) and proceeds to the next assessment module.

FIG. 5D illustrates the dietary assessment module. Initially a determination is made (step 262) as to whether the dietary assessment module is enabled. If enabled, the program determines which form of dietary assessment is to be used. Three forms of assessment are possible: food intake, caloric intake, and food exchange. The display 12 prompts the patient to enter only the physician-specified assessment information pertaining to their diet.

If the food intake module is enabled (step 264), the display prompts the patient, "FOOD INTAKE (1-5)?" (step 266). After entering a food intake value of 1 to 5, the algorithm proceeds to the next assessment module. Alternatively, if the caloric intake assessment is prescribed as determined in step 268, the algorithm prompts the patient, "DIET CALORIES: E" (step 270). The patient then enters a caloric value and the algorithm proceeds to the next assessment module.

As a third alternative, the physician may require the patient to use the food exchange system of the American Dietetic Association to assess dietary intake. If this module is enabled o (step 272), the patient is asked, "ATE EXPECTED FOOD Y/N?" (step 274). If the patient responds with a NO, the program module proceeds in step 276 to prompt the patient to enter correct exchanges for each food exchange category (milk, vegetable, fruit, bread, meat and fat). Upon entering correct exchanges, or if a YES was entered in step 274, the program proceeds to display food value for last quarter (step 278). As illustratively shown, Food Value Last Quad 278 shows carbohydrates at 32 grams, fat at 12 grams, protein at 7 grams, and calories at 342. After displaying these values, the program proceeds to the next assessment module.

If, however, in response to the prompt in step 274, the patient responds by pressing RD (REVIEW DATA), then in step 275, the program will display the patient's prescribed food values. The patient should then be able to determine the appropriate answer to the question "ATE EXPECTED FOOD Y/N?," after which the program returns to step 274 and reprompts the patient.

Figure 5G:
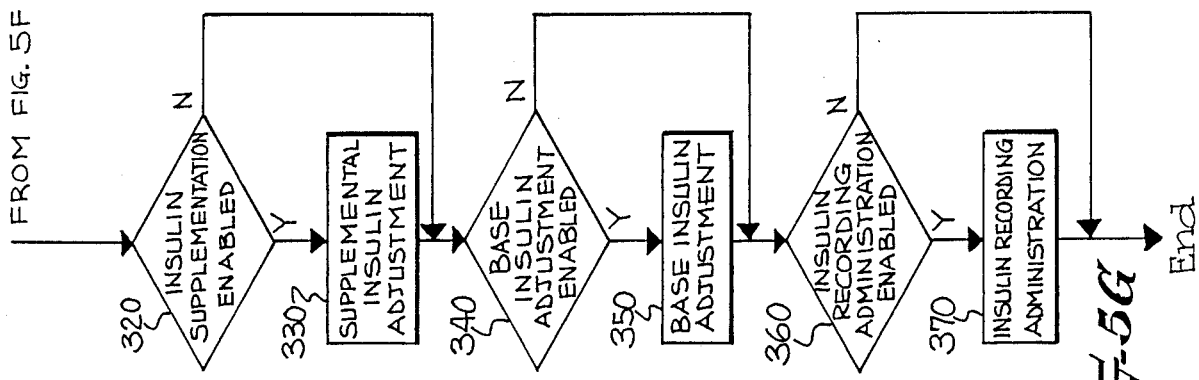
FIG. 5G is a functional flow chart illustrating the sequence of the insulin supplementation, basal insulin adjustment, and insulin recording/administration firmware modules.
Figure 5F:
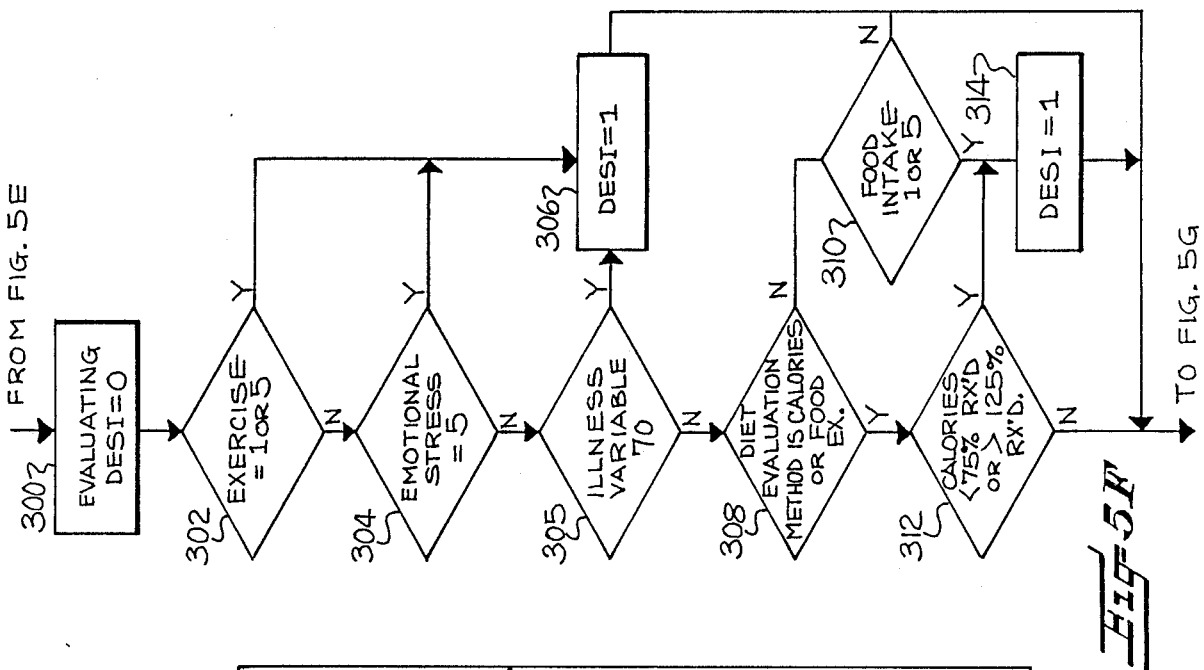
FIG. 5F is a functional flow chart illustrating the diet, exercise, stress, illness (DESI) data evaluation firmware module.
Figure 5E:
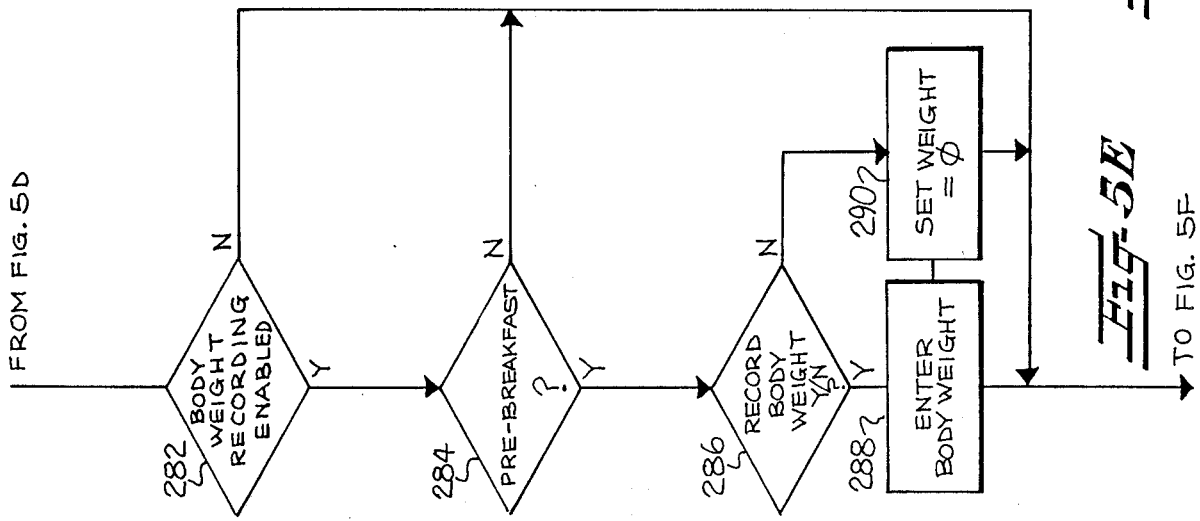
FIG. 5E is a functional flow chart illustrating the body weight recording firmware module.

FIG. 5E is a flow chart illustration of the body weight recording program module. First, a determination is made in step 282 as to whether the module is enabled. If enabled, then in step 284, the program module determines whether the relative recording time, entered by the patient in step 202 (FIG. 5A) was PREBREAKFAST. If so, the display prompts the patient "RECORD BODY WEIGHT Y/N?" (step 286). If not, then the program exits the module.

Upon entering a NO in response to the prompt of step 286, the program module sets the patient's body weight to "0" (step 290). If the patient enters a YES, then the program module prompts the patient to enter body weight in step 288. After this entry in step 288, or alternatively setting weight equal to zero in step 290, the program exits the body weight recording module and proceeds to the first step of FIG. 5F.

The flow chart of FIG. 5F illustrates the program steps for determining whether the patient's diet, exercise, and stress are within a normal range or whether the patient is ill. First, in step 300, the monitor displays the message "EVALUATING". This display continues while the following steps are executed. Also in step 300, the variable DESI, representing diet, exercise, stress, and illness, is initialized to "0" indicating that diet, exercise, and stress, are within normal limits, and the patient is not ill. In the steps that follow, significant changes in the patient's normal pattern of diet or exercise, a substantial amount of emotional stress, or a reported illness will cause the DESI variable to be set to "1".

Step 302 determines whether the exercise value entered in step 244 (FIG. 5C) is equal to "1" or "5". If the amount of exercise is either substantially less than usual (1) or substantially more than usual (5) for this time of day, then in step 306, DESI is set to "1". Otherwise, the program continues to step 304. Step 304 determines whether the emotional stress value entered previously in step 248 (FIG. 5C) is equal to "5", indicating substantially more stress than usual for this time of day. If so, DESI is again set to "1"; otherwise, the program continues with DESI unchanged. Step 305 determines whether the illness variable in FIG. 5C is greater than zero. If so, indicating the patient is now ill, then in step 306, DESI is again set to "1".

In step 308, before checking the patient's diet, the program first determines whether the patient uses calories or food exchanges to record dietary intake. If the calorie assessment program module is enabled in step 268 (FIG. 5D), then the patient uses calories to measure intake. If the food exchange assessment module is enabled in step 272, then the patient uses food exchanges. If neither is enabled, then it is assumed that the patient records dietary intake on a "1-5" scale as provided in the food intake assessment module in steps 264-266.

Thus, if the patient uses either calories or food exchange values, the number of calories is tested in step 312 to see if it is within 25% of the prescribed amount. The number comes from either the patient's entry in step 270, or as calculated in the food exchange assessment program module in step 278. If the food intake measured in calories is outside the 25% range in step 312, then in step 314 DESI is set to "1", else it remains unchanged.

If the patient records food intake on a "1-5" scale, then in step 310, the food intake value entered previously is tested to see if it is equal to "1" or "5", indicating none or almost no food for that meal or snack (1) or much more than usual (5). If food intake is either "1" or 5" in step 314 DESI is set to "1" and the program proceeds to step 320.

As shown in FIG. 5G, a determination is made in step 320 as to whether the supplemental insulin adjustment program module is enabled. This module may be enabled for a particular patient according to the prescription entered by the physician, or it may be disabled only for certain entry times during the day such as when the patient is not scheduled to take any insulin.

The supplemental insulin adjustment module shown in step 330 operates on pre-meal blood sugar values only. When a high blood sugar (hyperglycemia) results from a recent substantial change in one of the management variables of diet, exercise, stress, or illness (DESI), then the program module will calculate a supplemental dose of short acting (regular) insulin to correct the hyperglycemia. Step 330 is further described in reference to the flow chart diagrams of FIGS. 6A-6C which illustrate the program steps for determining whether a supplement is needed and for calculating a supplemental dosage.

Step 340 determines whether the base insulin adjustment program module is enabled for this patient at this time. Base insulin refers to the insulin that is scheduled to be taken at a pre-meal entry time. A single "target" insulin is selected for adjustment according to the pre-meal entry time. The target insulin is identified as the one most affecting the current blood sugar. The base insulin adjustment program module of step 340 will adjust the target insulin dosage based upon consistent blood sugar patterns. FIGS. 7A-7H contain flow chart diagrams which further illustrate the program steps embodied in step 340 for adjusting the base insulin.

Finally, in step 360, the program determines whether the insulin recording/administration program module is enabled. This module may be disabled if the patient is not scheduled to take any insulin at this entry time. If it is enabled, then the insulin recoding/administration module shown in step 370 calculates the total insulin dosage and provides prompts to the patient on the monitor display. The program module depicted in step 370 is further illustrated in the flow chart diagrams of FIGS. 8A–8F to be described subsequently.

Figure 6B:
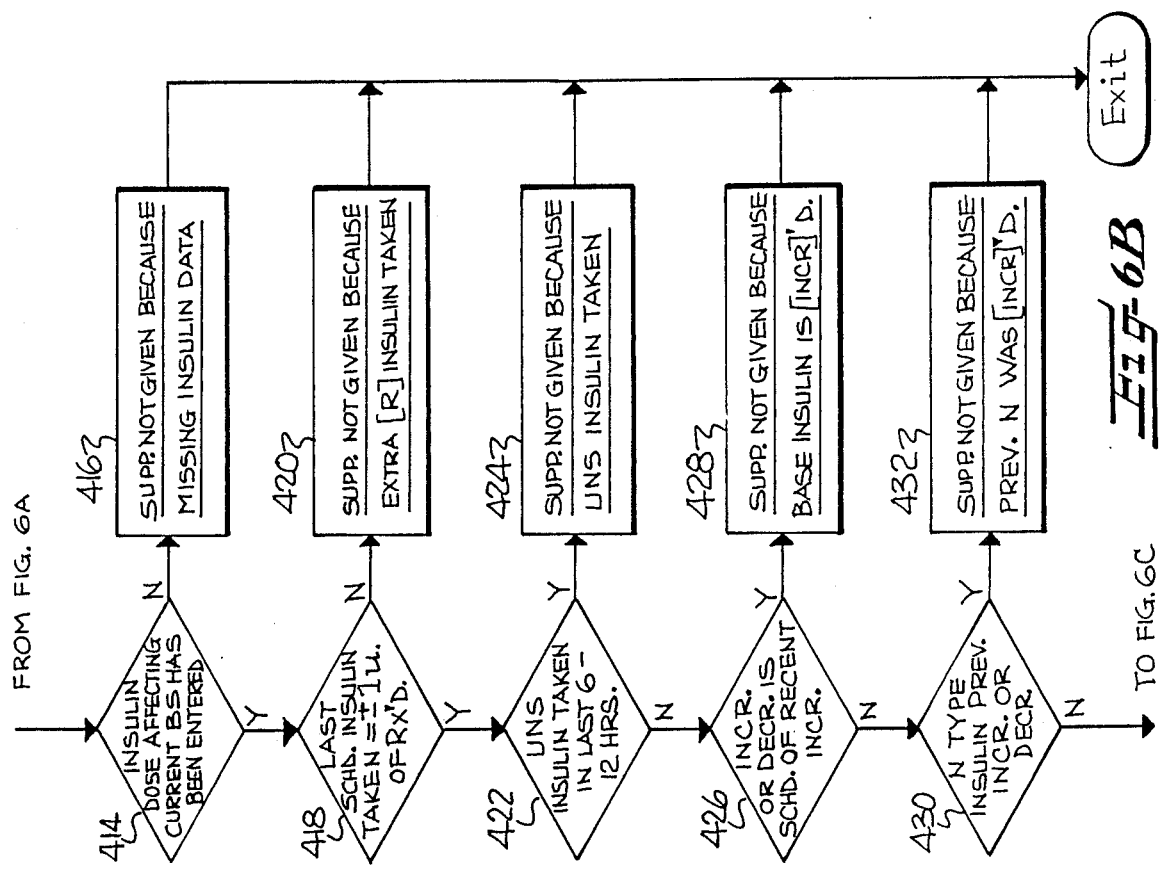
FIGS. 6A-6C taken together, are a functional flow chart diagram of the supplemental insulin adjustment firmware module.
Figure 6A:
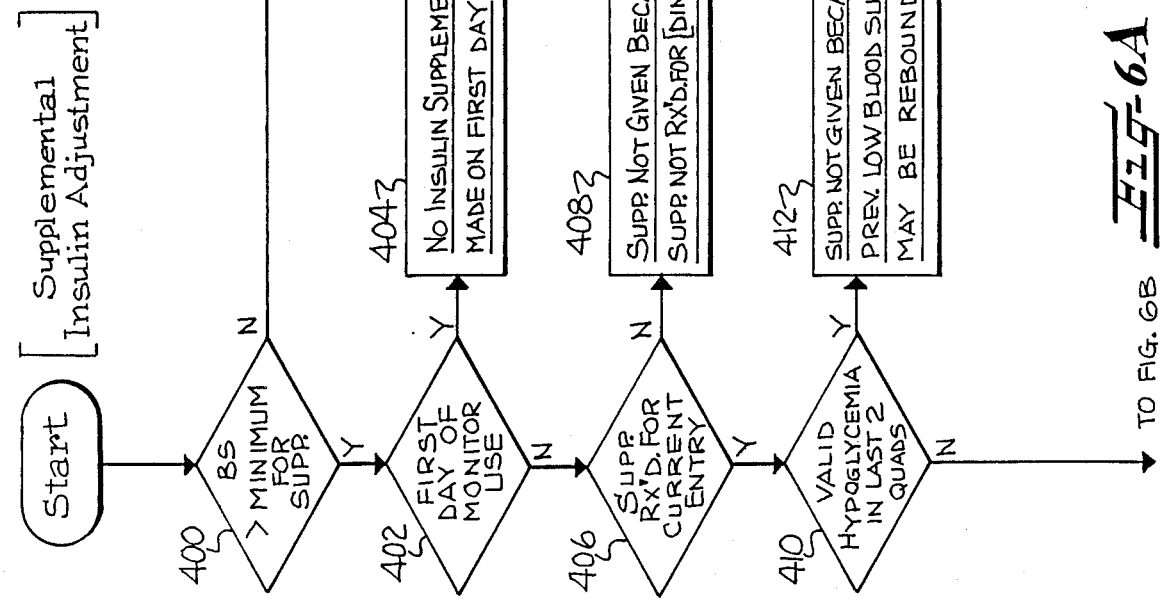
Figure 6C:
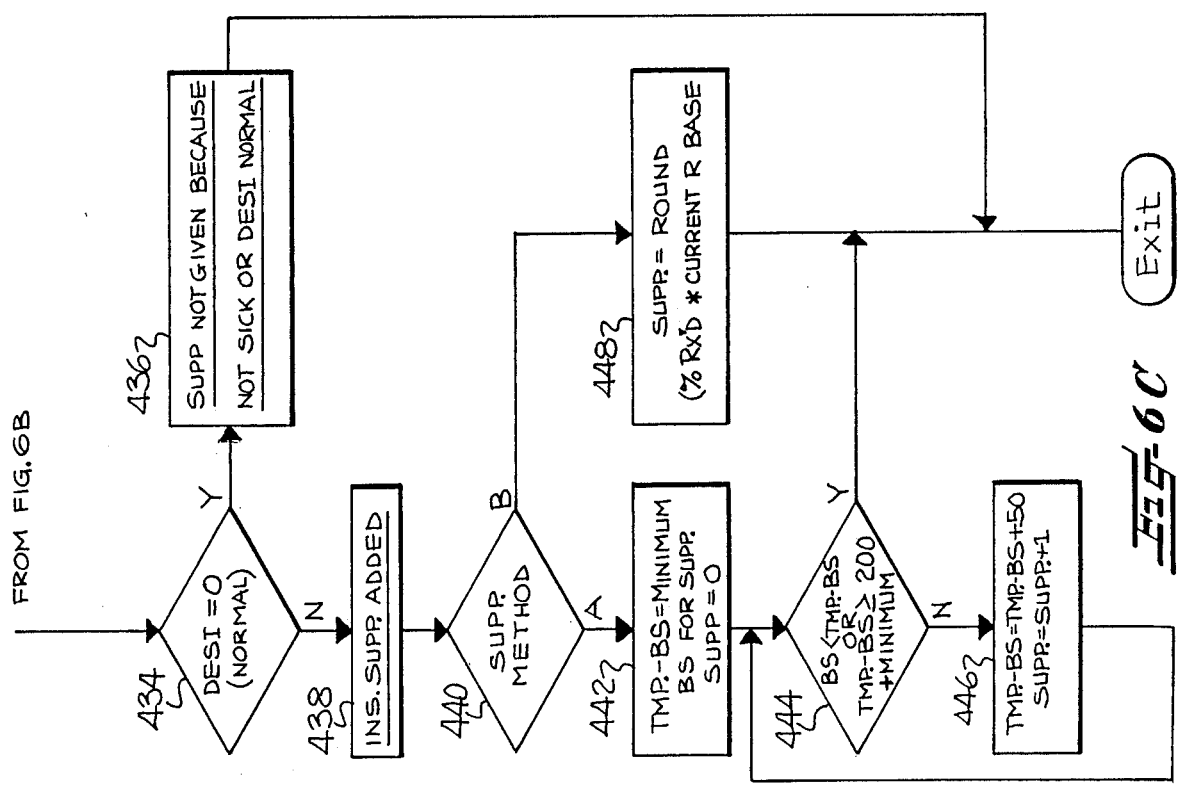

FIGS. 6A–6C taken together are a functional flow chart diagram of the supplemental insulin adjustment program module shown in step 330 (FIG. 5G). When high blood sugar results from a substantial change in the patient's diet, exercise, stress, or illness (DESI), the program module will suggest a supplemental dose of short acting regular insulin. The suggested dose will either be one unit of short acting insulin increased by one unit for each 50 mg/dl increment in the blood sugar over a set limit or a percentage of the current R base insulin. The limit at which a supplement will be suggested is normally set at a blood sugar value of 200 mg/dl, but it may be changed according to an individual patient's prescription.

If the patient has not entered enough information about insulin, blood sugar, or other control factors, or if the patient has taken an unusual or non-prescribed dose of insulin which could effect the current blood sugar, the program module will not attempt to calculate a supplement. Instead, a message will be provided on the monitor display to let the patient know why a supplement was not suggested. Also, the supplemental insulin adjustment module will prevent an overlap in insulin activity due to supplemental insulin doses. For example, a recent increase in base insulin will cancel a supplement at the next meal.

In reference to FIG. 6A, the first step in the supplemental insulin adjustment module, step 400, determines whether the current blood sugar (BS) exceeds the minimum level for which supplement is given. The minimum is generally set at 200 mg/dl but may vary for individual patients. If the current blood sugar is less than the minimum for supplementation, then the program module is exited via the N branch of step 400.

The steps that follow, namely steps 402–436, test for certain conditions before a supplement is suggested. If any of these conditions are not met, then a message is provided to the patient as to why a supplement is not recommended and execution of the supplemental insulin adjustment module is terminated.

In step 402, the program module checks to see if this is the first day the patient has used the monitor. No insulin adjustments are allowed until the patient has been using the monitor for one full day because there is not enough information to prescribe a supplement. If this is the first day of monitor use, the program module displays the message "NO INSULIN SUPPLEMENTATION MADE ON FIRST DAY" (step 404) and exits. Otherwise it continues to step 406.

Step 406 determines whether a supplement is prescribed for the patient for this particular entry time. If not, then the message "SUPP NOT GIVEN BECAUSE SUPP NOT RX'D FOR DINNER" (step 408), for example, is displayed with the current entry time.

Step 410 checks the last two quadrants (e.g., if the current entry time is "DINNER", it will check the previous "LUNCH" and "BREAKFAST" entries) to see whether the patient has recorded a valid hypoglycemic condition. The "valid hypo" flag is set whenever the patient has reported hypoglycemia symptoms (see steps 204–210 in FIG. 5A) with concurrent low blood sugar below a predetermined limit. This flag is also set if hypoglycemia symptoms alone were recorded during sleep. Symptoms sufficient to cause waking are in a sense "self-validating." Step 410 is necessary because when the blood sugar level drops too low, it may rebound to a level above normal. In other words, the low blood sugar may be caused by too much insulin, so it is unwise to give more insulin until the blood sugar stabilizes again. Thus, if step 410 detects a previous valid hypo, then the message "SUPP NOT GIVEN BECAUSE PREV. LOW BLOOD SUGAR MAY BE REBOUND" is displayed and the program module exits.

Step 414 (FIG. 6B) checks the patient's previous data entry for the most recent scheduled dose of insulin. The supplemental insulin adjustment program module will suggest an insulin supplement only if the insulin dose affecting the current blood sugar has been entered. If not, the program will display the message "SUPP NOT GIVEN BECAUSE MISSING INSULIN DATA" (step 416) and then exit.

In step 418, the program module tests the amount of insulin taken at the last pre-meal entry time to determine whether it was within one unit of that prescribed. If the patient took more NPH, semi-lente, or regular insulin than was scheduled, the effect of that extra insulin could overlap with a supplement given now. Therefore, the supplement is cancelled and in step 420, the message "SUPP NOT GIVEN BECAUSE EXTRA R INSULIN TAKEN" is displayed, for example, indicating the type of isulin. Also, if the patient took an unscheduled (UNS) dose of regular or NPH insulin during the past six to twelve hours, then the effect of that extra insulin may overlap with a supplement at this entry time. Step 422 checks for unscheduled insulin, and if found, the message "SUPP NOT GIVEN BECAUSE UNS INSULIN TAKEN" (step 424) is displayed.

Step 426 determines whether the regular base insulin for this entry was recently increased or is going to be increased or decreased. An increase in base insulin cancels a supplement at this entry time for three days while the increase is being tested. A scheduled decrease in insulin cancels a supplement at this entry time only. Thus, if either of the conditions of step 426 are met, then in step 428, the program displays the message "SUPP NOT GIVEN BECAUSE BASE INSULIN IS INCR'd", for example, indicating whether the base insulin was increased (INCR'd) or decreased (DECR'd). Similarly, step 430 determines whether the NPH insulin most recently taken was increased or decreased. If so, the message "SUPP NOT GIVEN BECAUSE PREV. N WAS INCR'd" (step 432) is displayed with either an increase (INCR'd) or decrease (DECR'd) indicated.

Step 434 (FIG. 5C) tests the DESI variable which was set in steps 300–314 of FIG. 5F. Insulin supplements are prescribed only during illness or substantial changes in diet, exercise, or stress Thus, if DESI=0 (normal) than a supplement will not be given and the message "SUPP NOT GIVEN BECAUSE NOT SICK OR DESI NORMAL" (step 436) is displayed. If DESI=1 (abnormal), however, then in step 438, the monitor will display the message "INS SUPP NEEDED".

Steps 440–448 calculate the supplemental dosage according to either of two methods. Step 440 will first determine which method is prescribed by the physician for this particular patient. The first method (A), steps 442-446, calculates the supplement based on 50 mg/dl increments in the current blood sugar over the minimum blood sugar for a supplement. In step 442, a temporary variable TMP-BS is set equal to this minimum, generally 200 mg/dl. The supplement value (SUPP) is set to zero. Step 446 tests the current blood sugar (BS) against the variable TMP-BS and TMP-BS against the minimum blood sugar for a supplement plus 200. If either the current blood sugar (BS) is less than TMP-BS or TMP-BS is greater than 200 plus the minimum blood sugar, then the calculation of the supplement is complete. If not, then in step 446, TMP-BS is increased by 50 and SUPP is increased by 1. Thus, for each increment of 50 mg/dl in the current blood sugar over the minimum, SUPP will be increased by one unit.

The alternate method of calculating the supplement (B) shown in step 448 uses a prescribed percentage of the current R insulin base. The current R base is defined as the most recently scheduled base dose of R-type insulin. SUPP is determined by taking the prescribed percentage of the current R base and rounding it off to the nearest unit, but in no event less than one unit.

FIGS. 7A–7H taken together are a functional flow chart diagram of the base insulin adjustment program module shown in step 340 (FIG. 5G). The base insulin adjustment module operates on a single "target" insulin selected for adjustment according to the pre-meal entry time. For the most part, this single identified dose of insulin is considered, with relevant blood sugar and behavioral data, during adjustment.

When undesirable patterns of blood sugar values occur consistently and without apparent cause from substantial change in diet, exercise, emotional stress, or illness, the insulin dosage should be adjusted. Generally, a distinct pattern of consistently high or low blood sugar must occur for three days before any adjustment is attempted. If the patient has not entered enough information about insulin taken, blood sugar, or other control factors, or if the patient has taken an unusual or nonprescribed dose of insulin recently, the program module will not attempt to calculate an increase or a decrease in the identified base insulin. Instead, a message will be provided on the monitor display to let the patient know why the base insulin is unchanged.

In general, the base insulin adjustment module will suggest a decrease in insulin if the patient has a blood sugar value below a certain predetermined limit (usually 60 mg/dl) at approximately the same relative time for two days in a row, or if the patient has one occurrence of a blood sugar value less than 46 mg/dl. Decreases in base insulin are based on all low blood sugar values, even those which do not occur before meals. The target insulin will not be decreased if the low blood sugar was apparently caused by a substantial change in diet, exercise, emotional stress, or illness (DESI). Only one decrease in base insulin for any entry time will be suggested during a ten-hour period.

If a given pre-meal blood sugar value is consistently greater than a certain predetermined limit (usually 140 mg/dl) for three consecutive days at the same entry time without an apparent cause from a substantial change in diet, exercise, stress or illness, the program module will suggest an increase in the identified base insulin. Only one base insulin dosage increase will be suggested during a three-day period to avoid a possible overlap in insulin activity and to allow time to assess the effects of one change before a second change is made. Also, before the program will try to correct an elevated fasting (i.e., pre-breakfast) blood sugar pattern, the patient will be prompted to perform a 3:00 A.M. blood sugar test. The relevant base insulin dose will then be increased or decreased depending on the results of the 3:00 A.M. blood sugar.

Figure 7A:
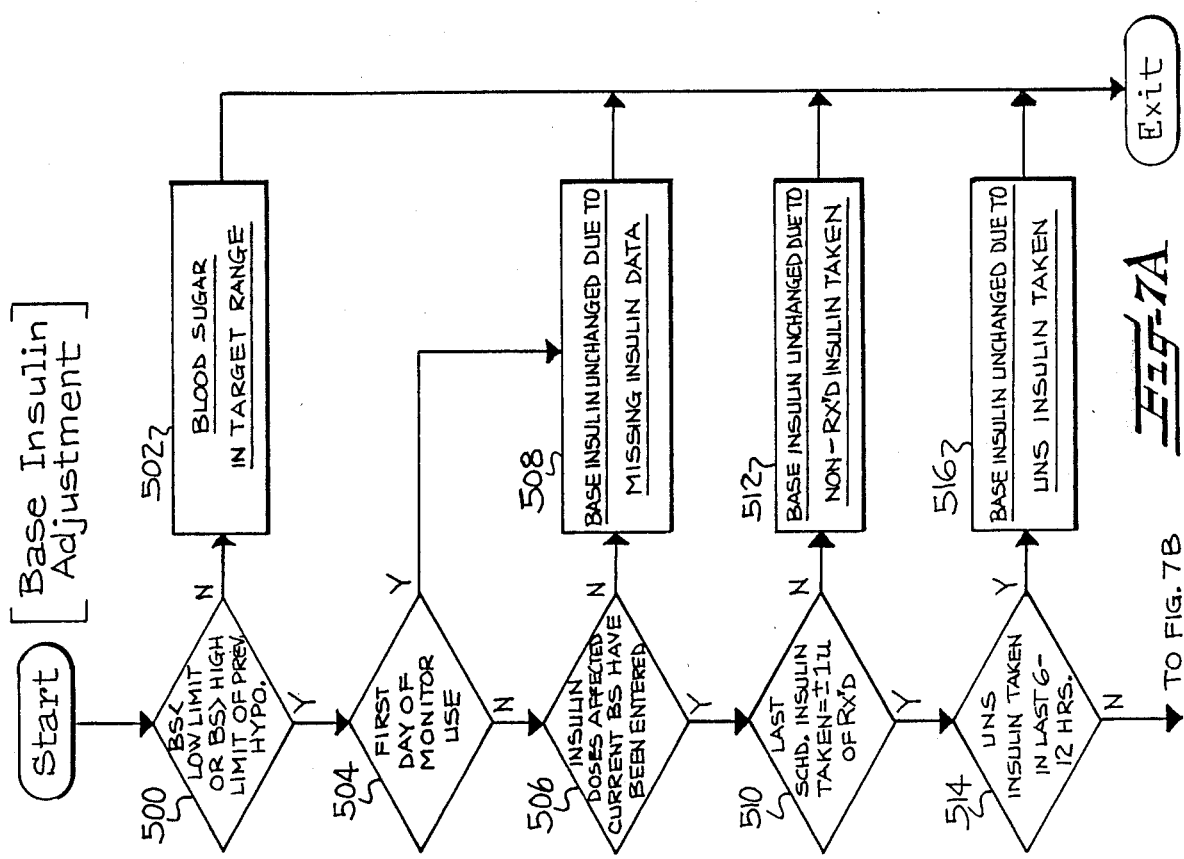

In reference to FIG. 7A, step 500 first determines whether any adjustment in the target base insulin is required. One of three possible conditions must be met: either (1) the current blood sugar is below a prescribed lower limit; (2) the current blood sugar is above a prescribed upper limit; or (3) the patient has recorded a valid hypoglycemia since this entry time on the previous day. A "valid hypo" is generally defined as both reported hypoglycemia symptoms (see steps 204–210 in FIG. 5A) with concurrent low blood sugar below a predetermined limit but, as noted previously, the "valid hypo" condition may also be set if hypoglycemia symptoms alone were recorded during the night. If none of the conditions are met, then in step 502, the message "BLOOD SUGAR IN TARGET RANGE" is displayed and no adjustment to the base insulin is required.

The steps that immediately follow, namely steps 504≧522, test for certain conditions before an increase or decrease to the target base insulin is suggested. If any of these conditions are not met, then a message is provided to the patient as to why an increase or decrease is not indicated.

In step 504, the program module checks to see if this is the first day the patient has used the monitor. No insulin adjustments are allowed until the patient has been using the monitor for one full day because there is not enough information to make adjustments. If this is the first day of monitored use, the program module displays the message "BASE INS UNCHANGED DUE TO MISSING INSULIN DATA" (step 508) and then exits.

Step 506 checks the patient's previous data entry for the target base insulin, which is normally the most recently scheduled dose of insulin. The base insulin adjustment program module will adjust the base insulin only if the insulin dose affecting the current blood sugar has been entered. If not the program will display the same message in step 508 and then exit.

In step 510, the program module tests the amount of insulin taken at the last pre-meal entry time to determine whether it was within one unit of that prescribed. If the patient took more or less insulin than was scheduled, the effect of that altered insulin dose may interfere with assessment of the current scheduled dose. In step 512, the message "BASE INSULIN UNCHANGED DUE TO NON-RX'D INSULIN TAKEN" is displayed if the patient took non-prescribed insulin. If the patient took an unscheduled (UNS) dose of regular, semi-lente, NPH, or lente insulin during the last six to twelve hours, then the effect of that extra insulin may also interfere with assessment of the prescribed insulin. Thus, step 514 checks for unscheduled insulin in the last six to twelve hours, and if found, the message "BASE INSULIN UNCHANGED DUE TO UNS IINSULIN TAKEN" (step 424) is displayed.

Step 518 (FIG. 7B) tests the DESI variable which is set in steps 300–314 of FIG. 5F. It is impossible to determine if the dose of insulin is correct if, at the same time, there are substantial changes in the patient's diet, exercise, stress, and illness. Therefore, no changes in base insulin are suggested unless DESI=0 (normal) for two days. In the step 520, the message "BASE INSULIN UNCHANGED DUE TO CHANGE IN DIET- /EX/ST/ILL" is given on the day that a substantial change in diet/exercise/stress/illness is noted, then on the following day "BASE INSULIN UNCHANGED DUE TO CHANGE IN DIET/EX/ST/ILL YESTERDAY" is displayed.

Step 522 checks for non-prescribed or missing insulin in the same manner as steps 510 and 514, only this time, the program looks at data at this entry time for the last two days. No decreases in the base insulin are recommended until a two-day pattern is established with a three-day pattern required for an insulin increase. If the data is not consistent for two days at this same time then the message "BASE INSULIN UNCHANGED DUE TO NON-RX'D OR MISSING INSULIN YESTERDAY" (step 524) is displayed.

If the program makes it this far without exiting, then in step 526, it is determined whether an increase or a decrease in the identified base insulin is generally indicated. If the current blood sugar is low, or the patient has reported a valid hypo, then the program continues, indicating a possible decrease. If neither condition is met, and thus the current blood sugar is high, then the program jumps to step 570 of FIG. 7E to further determine if an increase in the base insulin is needed.

If the current entry time is breakfast in step 528, then step 530 makes an additional check to see if the fasting (pre-breakfast) blood sugar has been high at this time for the last three days. In order to correct an elevated fasting blood sugar pattern, the base insulin adjustment program module executes a different set of steps shown in FIGS. 7G-7H before calculating an increase or decrease. Thus, the Y branch of step 530 will result in a jump to step 600 if the fasting blood sugar has been high for three days.

Continuing to step 532, this step begins a sequence of steps for determining whether the identified base insulin should be decreased. If a supplement was prescribed and taken in the previous quadrant (e.g., if the current entry time is "DINNER", the previous quadrant is "LUNCH") then the base insulin will not be decreased. It is assumed that if the current blood sugar is low and a supplement was prescribed and taken, the supplement was the cause of the low blood sugar. Thus, in step 532, if a supplement was taken, the program module will exit without changing the base insulin.

Usually, the base insulin adjustment program module will suggest a decrease in insulin only if the blood sugar is low at the same time for two days in a row. On a single occurrence of a blood sugar value less than 46 mg/dl, however, the program will recommend an immediate decrease. In step 534 (FIG. 7C) if the current blood sugar is less than 46 mg/dl or a previous hypo had a concurrent blood sugar less than 46, the program will skip steps 536-546 and go directly to step 550 (FIG. 5D) to calculate the decrease.

If in step 536, the base insulin was decreased at this same entry time on the previous day, then the base insulin will remain unchanged. In step 538, the base insulin adjustment program module also requires that the patient have either a low blood sugar or reported symptoms of hypoglycemia at this entry time on the day before in order to decrease the base insulin. If neither condition is met, then the message "BASE INSULIN UNCHANGED MUST HAVE 2 LO BS IN A ROW" (step 544) is displayed and the program exits.

As just described, either a low blood sugar or hypoglycemia symptoms alone on the previous day, with current low blood sugar or hypo symptoms, are generally sufficient to decrease the identified base insulin. If, however, the current entry time is breakfast, today's hypoglycemia symptoms must be validated by concurrent low blood sugar. Thus, if the current entry time is breakfast and the current blood sugar is not low in step 540, the hypo condition reported previously an this same day, either at the 3 AM test or at an unscheduled (UNS) time, must be validated. Step 542 validates the previous hypo by checking the blood sugar at the same entry time. If the "hypo" is not valid and there is no concurrent low blood sugar with the earlier recorded "hypo", the same messaage of step 574 is displayed and the program exits.

Step 546 determines whether there is sufficient base insulin prescribed from which to make a decrease. If the current insulin is greater than zero, and an increase is not currently being tested, then the program module will continue to calculate a decrease. Otherwise, the program will exit.

Step 550 (FIG. 7D) checks to see if any base insulin was decreased in the last 6-10 hours. In general, only like types of insulin separated by at least two quadrants (e.g., breakfast and dinner R type) or insulins separated by more than two quadrants (e.g., dinner R and the following lunch N) may be decreased consecutively. If a recent decrease is found in step 550, then the message "CANNOT DECR DINNER N INSULIN ONLY 1 DECR EVERY 6-10 HRS" (step 552), for example, is displayed, indicating the current entry time "DINNER", "LUNCH", etc., and the type of insulin, "R", "N", "S", or "L".

Step 544 indicates to the patient that all of the previous conditions for a decrease in base insulin have been met by displaying, for example, "NEXT DINNER N WILL DECR". Steps 556-564 then calculate the actual decrease in dosage. First, step 556 determines whether an increase in base insulin was previously prescribed in this quadrant. If so, then the base insulin will decrease by half the recent increase. Thus, in step 560, $\Delta$INS, the change in the base insulin, is set equal to the previous increase divided by two. If there was not an increase in the insulin identified affecting this quadrant's blood sugar pattern, then in step 558, $\Delta$INS is equal to 5% of the current base insulin rounded off to the nearest unit.

Finally, step 562 checks to see if this decrease is following a rebound pattern. A rebound is said to occur when the low blood sugar which prompted this decrease in base insulin is followed by an occurrence of high blood sugar. If so, the program module sets a "REBOUND" flag for the next three days to prevent any increases in the base insulin during this time. This flag is checked in step 582 (FIG. 7E) before an increase is suggested.

Returning to step 526 (FIG. 7B), if the blood sugar value is high, then an increase is generally indicated and the program will jump to step 570. Steps 570-590 (FIGS. 7E-F) make up the "increase" portion of the base adjustment program module.

First, in step 570, if the current entry time is breakfast, then the program module executes a different set of steps shown in FIGS. 7G-7H for evaluating a high fasting blood sugar pattern. Thus, the Y branch of step 570 will result in a jump to step 600.

Continuing if the current time is not breakfast, in step 572, the program determines whether the blood sugar has been high at this entry time for the last three days. An increase in base insulin will be recommended only if the given pre-meal blood sugar value is consistently higher than the upper limit for three consecutive days. If not, then the progam module exits without changing the base insulin.

Step 574 tests the DESI variable in the same manner as step 518, only this time, the program looks at data for the last three days. An increase in the base insulin is not recommended unless DESI=0 (Normal) for three days. In step 575, the message "BASE INSULIN UNCHANGED DUE TO CHANGE IN DIET/EX/ST-/ILL TWO DAYS AGO" is displayed if a substantial change is found two days previous.

Similarly, step 576 checks for non-prescribed or missing insulin data over a three-day period. A three-day pattern is reguired before an insulin increase is recommended. If there is missing or non-prescribed insulin two days before this entry time, then the message "BASE INSULIN UNCHANGED DUE TO NON-RX'd OR MISSING INSULIN TWO DAYS AGO" (Step 577) is displayed.

Furthermore, only one increase in base insulin dosage will be suggested during a three day period to avoid a possible overlap in insulin activity and to allow time to assess the effects of one change before a second change is made. Thus, in step 578, if it is less than three days since the last increase, the message "MUST HAVE 3 DAYS BETWEEN INSULIN INCR'S" (step 580) is displayed.

Step 582 tests to see if the REBOUND flag has been set by step 562 (FIG. 7D). A rebound pattern detected by step 562 will disable any increases for the next three days by setting this flag. If the REBOUND flag is set, then in step 582, the program exits without an increase.

In step 584, the monitor will display, for example, the message "NEXT DINNER N WILL INCR" indicating the entry time "DINNER", "LUNCH", etc., and the type of insulin, either "N" or "R". Steps 586-590 then calculate the actual increase in the base insulin, INS.

Step 586 sets a temporary variable TMP-BS to the upper limit of the blood sugar value at which an increase is recommended, usually 140 mg/dl. A pointer variable P is set to zero. Step 588 tests the current blood sugar (BS) against the variable TMP-BS and TMP-BS against the upper limit for any increase plus 250. If either BS is less than TMP-BS or TMP-BS is greater than 250 plus the high limit, then the calculation is completed in step 590. If not, then in step 592, TMP-BS is increased by 50 and P is increased by 1. Thus, for each increment of 50 mg/dl in the current blood sugar over the upper limit, P will be increased by 1. P is then used to identify one of several prescribed percentages dependent on the range of the current blood sugar.

INS is determined in step 590 by taking the prescribed percentage of the current base and rounding it off to the nearest unit.

In order to correct an elevated fasting blood sugar pattern, the program module will execute the steps shown in FIGS. 7G-7H before calculating an increase or decrease. The patient will be prompted to perform a 3:00 a.m. blood test and the base insulin dose will be increased or decreased dependent on the results of the 3:00 a.m. test. In step 600, the program module will determine whether the pre-breakfast blood sugar has been high for the past three days. A change in insulin will be recommended at breakfast only if the fasting blood sugar value is consistently higher than the predetermined limit for three consecutive days. If not, then the program exits without changing the base insulin.

In step 602, DESI is tested for an expanded three-day period as in step 574 (FIG. 7E). The appropriate message is displayed in step 603 if DESI=0 (abnormal) during this period. Similarly, step 576 checks for missing or non-prescribed insulin and a message is displayed in step 577.

Step 606 determines whether there has been at least two days since any prior fasting decrease in base insulin. This is to allow time to assess the effects of one change before a second change is made. In step 608, the program module checks to see if the patient made a 3:00 a.m. entry today. A 3:00 a.m. measure is always required before a fasting insulin can be adjusted. If not, the patient is prompted to perform a 3:00 a.m. blood sugar test the following day in step 610. If the patient has done a 3:00 a.m. test, then step 612 will display the result.

Step 614 tests the 3:00 a.m. blood sugar value to see if it is greater than 99 mg/dl. Generally, if hypoglycemia symptoms are sufficient to wake the patient, then the symptoms are probably indicative of a low blood sugar. If any objective measure of the blood sugar at the same time contradicts this, however, i.e., blood sugar greater than 99, then the hypoglycemia value will be invalidated and reset to zero. This is because patient-reported symptoms of hypoglycemia are often unreliable and may actually be only a result of a drop from a high blood sugar level to a normal level. Therefore, if there is no concurrent low blood sugar, the hypo is invalidated in step 616.

In step 618, if it is less than three days since the last increase, the message "MUST HAVE 3 DAYS BETWEEN INSULIN INCRS" (step 620) is displayed. This is because only one increase in base dosage is allowed during a three day period to avoid a possible overlap in insulin activity and to allow time to assess the effects of one change before another is made. Finally, in step 622, a decision is made based on the 3:00 a.m. blood sugar test as to whether an increase or a decrease in base insulin is indicated. If the 3:00 a.m. blood sugar is less than 100, then the program module jumps back to step 550 (FIG. 7D) and continues to calculate a base insulin decrease. If the 3:00 a.m. blood sugar is greater than or equal to 100, then the program returns to step 582 (FIG. 7E) and the steps that follow to calculate an increase in base insulin.

FIGS. 8A-8F taken together, are a functional flow chart diagram of the insulin recording/administration program module shown in step 360 (FIG. 5F). The insulin recording/administration module calculates the total insulin dosage for this entry and provides prompts to the patient on the monitor display. FIG. 8A illustrates the main functions of the recording/administration program module. FIGS. 8B-8D illustrate a subfunction of the program module called by the main routine in FIG. 8A for computing the insulin dosages. FIGS. 8E-8F illustrate another subfunction called by both the main routine and the computation subroutine for checking the patient's data entry of insulin taken.

First, in step 700, the insulin recording/administration program module determines whether this is an unscheduled (UNS) entry. If it is unscheduled, then the insulin to be taken is merely recorded. Step 701 asks the patient "TAKE INSULIN NOW - Y/N?" If YES, then in step 702, the patient is prompted for each of two types of insulin used by the patient, for example, "R INSULIN <E>" and "N INSULIN <E>." The patient will then enter the actual dose of each insulin taken and press the ENTER key. The program module will record and then check the patient's entry for miskeys only by executing the steps illustrated in FIGS. 8E-8F. After this, the program module will exit and the sequence for this entry time is complete.

If this is not an unscheduled entry, then step 704 determines whether the patient needs to take any insulin now during this scheduled (SCH) entry. Step 704 will check to see if there is any R base insulin to be taken (Rb greater than zero), any N base insulin (Nb greater than zero), a supplement (SUPP greater than zero), a change in R base insulin ($\Delta R$ not equal to zero) or a change in the N base insulin ($\Delta N$ not equal to zero). If none of these is present, then the patient is not to take any insulin and the program exits. Otherwise, the program continues to step 706.

Step 706 displays the message "INSULIN TO BE TAKEN" on the monitor display. Step 706 then calculates a preliminary total of each type of insulin to be taken for use in steps 708 and 712. The total R type insulin to be taken is equal to the R base plus any change in the R base (increase or decrease) plus any supplement. The total N type insulin to be taken is the N base insulin plus any change in the base. Step 708 determines whether the total R type insulin is greater than zero and thus there is R type insulin to be taken at this time. If R is positive, then in step 710, the steps shown in FIGS. 8B-8D are executed for the R type insulin to calculate the total R insulin and provide prompts to the patient. Similarly, if N is positive in step 712, the same steps in FIGS. 8B-8D are executed for the N type insulin in step 714. After these steps, the program module will exit and the sequence for this entry time is complete.

FIGS. 8B-8D taken together illustrate the subfunction of computing the insulin doses executed in steps 710 and 714 of FIG. 8A. The steps shown in FIGS. 8B-8D are executed for both R and N types of insulin.

Step 720 determines whether only a supplement is to be given. If both the base insulin and the change in insulin are zero, then there must be a supplement. This will be the case only for R type insulin, however, because N type supplements are not considered possible. Thus, in step 722, the insulin dose will be set equal to the supplement only and the monitor display will read "R SUPPLEMENT 2 <E>", for example. After the patient enters the actual dose taken, the program module will record and then check the entry by executing the steps shown in FIGS. 8E-8F.

If in step 724, the supplement is greater than zero, then the insulin to be taken is the base insulin plus the supplement. Again, this is only possible for R type insulin and there will never be both an increase and a supplement prescribed at the same time. The patient is prompted, for example, "R W/SUPP 5+1=6 <E>" as shown in 726. The patient's entry is recorded and checked by the steps in FIGS. 8E-8F.

If in step 728, the change in insulin is greater than zero, then the patient is obviously scheduled for an increase in base insulin. Steps 730-734 are "housekeeping" steps to allow the patient to test an increase in base insulin over three days before the base insulin is permanently changed. In step 730, the variable DAYS measuring the number of days since the increase was first scheduled is incremented by 1. If in step 732, DAYS is equal to 4, then the patient is beyond the three days since the original increase and this must be a new change in the base insulin. As described previously, only one increase in base insulin is made in a three day period to avoid possible overlap in insulin activity and allow time to assess its effects before a second change is made. If DAYS is equal to 4, then it is reset to zero in step 734. The DAYS variable is used subsequently in step 752 to decide whether to make the increase to base insulin permanent on the third day of testing.

In step 736, if the change in insulin is zero, meaning that there is no increase or decrease in the base insulin, then in step 738 the insulin to be taken is equal to the base. The patient is prompted "R INSULIN 5<E>", for example, and the patient's entry is recorded and then checked by the steps in FIGS. 8E-8F. Following step 738, the insulin computation subfunction is complete and the program module sequence of execution will return to the main routine of FIG. 8A.

In step 740 (FIG. 8C), since the change in insulin is not zero (step 736), the insulin to be taken must be equal to the base plus the change—either an increase or a decrease. If, in step 742, the total insulin is less than zero, then step 744 will set the amount of insulin to be taken to zero. The patient can obviously never take a negative dose and this prevents the program from giving the patient a prompt with a negative value.

Step 746 determines whether an increase or a decrease in base insulin is scheduled. If the change in insulin is negative, then step 750 for giving and recording a decrease is executed. Otherwise, if the change in insulin is positive, then an increase is given in step 748 and those steps that follow.

In step 750, the message "R W/DECR 5−1=4 <E>", for example, is displayed. The patient's entry is recorded and then checked as in previous steps. The change to the base insulin is then made effective by setting it equal to the current base plus the change. Since the change is in fact negative, i.e., $\Delta INS$ is less than zero, the base insulin will be decreased. The change in insulin is then reset to zero.

In step 748, a message such as "R W/INCR 5+1=6 <E>" is displayed indicating an increase in base insulin. The patient's entry of insulin actually taken is recorded and then checked. An increase to the base, however, is not made immediately. The patient will be instructed that he is taking an increase, but the base insulin will not be permanently changed until the end of a three-day testing period. Thus, if DAYS is not equal to "3" in step 752, the insulin computation subfunction is complete and the program will return to the main routine of FIG. 8A. If this is the third day, however, the additional steps 754-764 will be executed before returning.

Step 754 calculates a three-day average for the insulin actually taken at this time. In step 756 (FIG. 8D), the three-day average is compared to the insulin that was to be taken at this entry time including the increase. If the patient has taken less insulin than was suggested for the last three days, then in step 758, the message, for example, "3 DAY AVE R DOSE=5" is displayed, to inform the patient that he has taken less than the recommended increase during the last three days. In step 760, the patient will be asked whether he wants to make his base insulin equal to the three-day average rather than the greater recommended amount by displaying, for example, the message "MAKE R=5 NOT 6 Y/N?". If the patient responds YES then the base insulin is set to the three-day average. The program has, in effect, "learned" a lesser dose of insulin based on the patient's responses. If the patient is being too conservative in not accepting the recommended increase, however, the base adjustment program module will subsequently recommend another increase to the base dose.

If the patient rejects the three-day average in step 760, or the three-day average is the same as the current insulin because the patient took the recommended amount in step 756, then step 762 will be executed. In step 762, the change to the base insulin is made by setting it equal to the current base plus the change. Since the change is positive, i.e., ΔINS is greater than zero, the base insulin will be permanently increased. The change in insulin is then reset to zero and the program returns to the main routine.

The steps shown in FIGS. 8E–8F are executed each time after the patient is prompted to take a dose of insulin and has entered the actual amount taken. The program module subfunction illustrated in steps 770–792 checks the patient's data entry for possible keying errors and to notify the patient if he has taken a non-prescribed dose of insulin. In step 770, the insulin taken is the amount the patient keyed in before he pressed ENTER. In the following steps, this amount is compared to the amount of insulin actually prescribed by the program.

In step 772, if the insulin prescribed is not more than 8 units, or the difference (absolute value) between the insulin taken and that prescribed is not more than 2 units, then the program module skips steps 774–778. If both of these conditions are met, however, then steps 774–786 are executed for possible keying errors by the patient.

Steps 774 and 778 determine whether the amount of insulin taken was 25% more or less than that prescribed. If so, then the appropriate message is displayed, either "INSULIN DOSE GREATER THAN 125% EXPECTED" (step 776) or "INSULIN DOSE LESS THAN 75% EXPECTED" (step 780). The patient is then asked whether the amount he entered is actually the amount taken in step 784. If the response is NO, indicating the patient has made an error, the monitor display reprompts the patient in step 786 with the correct dose of insulin and allows the patient to re-enter the correct amount. The steps beginning with step 770 are then reexecuted to insure that no additional error is made. If the answer to step 784 is YES, then the program continues to step 788 (FIG. 8F). Similarly, in step 782, if this is an unscheduled (UNS) entry and the amount of insulin taken is greater than 9 units, the patient is given a chance to correct a possible mistake in step 784.

Steps 788–792 (FIG. 8F) notify the patient if a non-prescribed dose is taken. If the entry is unscheduled (UNS) in step 788, then the program module skips the next two steps. Otherwise, in step 790, the program checks to see whether the difference between the insulin taken and that prescribed is more than one unit. If so, then the message "NON-RX'D INSULIN TAKEN" (step 792) is displayed. The program then returns to either the main routine (FIG. 8A) of the insulin recording/administration program module or the appropriate step in the insulin computation submodule (FIGS. 8B–8D).

It will be apparent to those skilled in the art that the various modifications can be made to the home monitor system of the instant invention without departing from the scope or spirit of the invention, and it is intended that the present invention cover modifications and variations of the system provided they come within the scope of the appendant claims and their equivalents.

What is claimed is:

1. A method of monitoring a patient having diabetes mellitus with the use of a blood glucose measuring device and a thereto linked monitor apparatus capable of receiving and storing data, and of using the data to generate insulin dosage recommendations, comprising:
   (a) inputting initial physician-supplied data into the monitor apparatus;
   (b) supplying patient blood specimens at periodic times to the measuring device;
   (c) utilizing the measuring device to obtain blood glucose values from the specimens, and to effect automatic input into the monitor apparatus of glucose data representative of the glucose values;
   (d) utilizing the monitor apparatus to prompt and receive patient input into the monitor apparatus at periodic regular times of patient data relating to diet, exercise, emotional stress, and symptoms of hypoglycemia and other illness actually experienced by the patient during a preceding time period;
   (e) storing in the monitor apparatus the inputted physician, glucose and patient data;
   (f) utilizing the monitor apparatus to at times evaluate the data stored therein and to generate recommendations, based upon the evaluation, relative to patient insulin dosage.

2. A method as in claim 1, wherein the symptoms of illness include fever.

3. A method as in claim 1, wherein step (f) includes generating a recommendation relative to a supplemental insulin dosage.

4. A method as in claim 1, wherein the blood glucose measuring device is a reflectance photometer, and step (b) includes utilizing the monitor apparatus to prompt patient preparation of blood specimen test strips used in the photometer.

5. A monitor system adapted for use by a patient afflicted with diabetes mellitus, comprising:
   means for measuring blood glucose values and for generating blood glucose data in response to measuring said blood glucose values;
   monitor means, connected to said measuring means and capable of receiving, storing and evaluating data, for (a) receiving and storing said blood glucose data, (b) receiving and storing physician-supplied data, (c) prompting and receiving patient input into the monitor means at periodic times of patient data relating to diet, exercise, emotional stress and symptoms of hypoglycemia and other illness experienced by the patient during a preceding time period, (d) receiving and storing the patient data supplied by the patient, and (e) generating recommendations relative to patient insulin dosage based at least in part upon the received blood glucose data, physician data and patient data.

6. The monitor system as set forth in claim 5 wherein said measuring means includes:
   reflectance photometer means for measuring blood glucose values; and
   circuit means coupled to said reflectance photometer means for converting the output signals from said reflectance photometer means to glucose data.

7. The monitor system as set forth in claim 5 wherein the recommendations generated by said monitor means include a base insulin adjustment recommendation based at least in part upon said glucose data and said patient data stored in said monitor means over a prescribed number of days.

8. The monitor system as set forth in claim 5 wherein the recommendations generated by said monitor means include a supplemental insulin dose recommendation based at least in part upon said patient data and said glucose data stored in said monitor means.

9. The monitor system as set forth in claim 5 and further comprising:

computer means for at desired times receiving glucose data and patient data from said monitor means and for transmitting a physician insulin prescription to said monitor means;

and communication linkage means for at said times establishing a communication linkage between said computer means and said monitor means.

10. The monitor system as set forth in claim 9 wherein said linkage means includes modems associated with said monitor means and said computer means for receiving and transmitting data therebetween.

* * * * *